US012287323B2

(12) United States Patent
Piazza et al.

(10) Patent No.: US 12,287,323 B2
(45) Date of Patent: Apr. 29, 2025

(54) REPORTING CONSTRUCT WITH SYNAPTOBREVIN BASED MOIETY

(71) Applicant: BIOMADISON, INC., Del Mar, CA (US)

(72) Inventors: Timothy Piazza, McFarland, WI (US); Francis Mark Dunning, Madison, WI (US); Ward C Tucker, Monona, WI (US)

(73) Assignee: BIOMADISON, INC., Del Mar, CA (US)

( * ) Notice: Subject to any disclaimer, the term of this patent is extended or adjusted under 35 U.S.C. 154(b) by 525 days.

(21) Appl. No.: 17/583,594

(22) Filed: Jan. 25, 2022

(65) Prior Publication Data

US 2022/0196634 A1 Jun. 23, 2022

Related U.S. Application Data

(62) Division of application No. 15/597,002, filed on May 16, 2017, now Pat. No. 12,019,066.

(60) Provisional application No. 62/404,513, filed on Oct. 5, 2016, provisional application No. 62/336,964, filed on May 16, 2016.

(51) Int. Cl.
*G01N 33/50* (2006.01)
*C07K 14/435* (2006.01)
*C07K 14/705* (2006.01)
*C12Q 1/37* (2006.01)
*G06T 7/00* (2017.01)

(52) U.S. Cl.
CPC ... *G01N 33/5005* (2013.01); *C07K 14/43595* (2013.01); *C07K 14/705* (2013.01); *C12Q 1/37* (2013.01); *G06T 7/001* (2013.01); *G06T 7/0016* (2013.01); *C07K 2319/50* (2013.01); *C07K 2319/60* (2013.01); *C07K 2319/70* (2013.01); *G01N 2333/33* (2013.01); *G01N 2333/952* (2013.01); *G06T 2207/30072* (2013.01); *G06T 2207/30242* (2013.01)

(58) Field of Classification Search
CPC .......... G01N 33/5005; G01N 2333/33; G01N 2333/952; G01N 33/57407; G01N 33/57434; G01N 33/542; G01N 33/50; G01N 33/58; C07K 14/43595; C07K 14/705; C07K 2319/50; C07K 2319/60; C07K 2319/70; C12Q 1/37; G06T 7/001; G06T 7/0016; G06T 2207/30072; G06T 2207/30242

See application file for complete search history.

(56) References Cited

U.S. PATENT DOCUMENTS

| 6,100,234 A | 8/2000 | Huber |
| 7,094,888 B2 | 8/2006 | Miesenbock et al. |
| 8,969,016 B2 | 3/2015 | Fish et al. |
| 9,249,449 B2 | 2/2016 | Miyawaki |
| 9,274,121 B2 | 3/2016 | Atapattu |
| 9,453,254 B2 | 9/2016 | Tucker et al. |
| 9,624,529 B2 | 4/2017 | Oyler |
| 10,975,125 B2 * | 4/2021 | Tucker ................... C07K 14/00 |
| 11,661,442 B2 * | 5/2023 | Tucker ..................... C12N 9/52 |
| | | 435/23 |
| 2002/0110834 A1 | 8/2002 | Benkovic |
| 2002/0132327 A1 | 9/2002 | Hay |
| 2003/0059847 A1 | 3/2003 | Backes |
| 2003/0092629 A1 | 5/2003 | Tang |
| 2003/0100707 A1 | 5/2003 | Hwang |
| 2004/0038375 A1 | 2/2004 | Pedersen |
| 2004/0137597 A1 | 7/2004 | Davydov |
| 2004/0146938 A1 | 7/2004 | Nguyen |
| 2005/0074889 A1 | 4/2005 | Chumakov |
| 2006/0024289 A1 | 2/2006 | Ruggles |
| 2006/0105953 A1 | 5/2006 | Lacoste et al. |
| 2006/0134722 A1 | 6/2006 | Chapman et al. |
| 2007/0243565 A1 | 10/2007 | Williams et al. |
| 2008/0032917 A1 | 2/2008 | Li |
| 2008/0064054 A1 | 3/2008 | Fernandez-Salas |

(Continued)

FOREIGN PATENT DOCUMENTS

| WO | 2005076785 | 8/2005 |
| WO | 2006010106 | 1/2006 |

(Continued)

OTHER PUBLICATIONS

Welser, Katharina, et al. "Protease Sensing With Nanoparticle Based Platforms." Analyst (London. 1877. Online)/Analyst, vol. 136, No. 1, Sep. 2010, pp. 29-41. https://doi.org/10.1039/c0an00429d. (Year: 2010).*

(Continued)

*Primary Examiner* — Richard A Schnizer
*Assistant Examiner* — Amanda M Zahorik
(74) *Attorney, Agent, or Firm* — Fish IP Law, LLP

(57) ABSTRACT

Compositions and methods for improved cell-based methods of characterizing botulinum neurotoxins are provided. Cells utilized in these methods include a reporting construct that is cleaved following uptake and processing of botulinum neurotoxin by the cell, resulting in proteolysis of the portion of the reporting construct that is released following cleavage. The released portion includes a fluorophore and amino acid substitutions or sequences that enhance the rate of proteolysis. A pair of reporting constructs can be utilized in which one member of the pair is modified to resist cleavage by the botulinum neurotoxin while co-localizing with the remaining member of the pair.

11 Claims, 29 Drawing Sheets

Specification includes a Sequence Listing.

(56) References Cited

U.S. PATENT DOCUMENTS

| | | |
|---|---|---|
| 2009/0263836 A1 | 10/2009 | Fernandez-Salas |
| 2010/0034777 A1 | 2/2010 | Wandless |
| 2010/0086930 A1 | 4/2010 | Soukka |
| 2011/0165191 A1 | 7/2011 | Ranga |
| 2011/0269141 A1 | 11/2011 | Murayama |
| 2012/0322092 A1 | 12/2012 | Tucker et al. |
| 2014/0024063 A1 | 1/2014 | Piazza et al. |
| 2014/0249295 A1 | 9/2014 | Bonger |
| 2014/0255361 A1 | 9/2014 | Wandless |
| 2014/0323391 A1 | 10/2014 | Tsalik |
| 2015/0010931 A1 | 1/2015 | Oyler et al. |
| 2015/0118701 A1 | 4/2015 | Tucker |
| 2015/0159193 A1 | 6/2015 | Tucker et al. |
| 2015/0315574 A1 | 11/2015 | Wilusz |
| 2015/0329896 A1* | 11/2015 | Oyler .................. C12Q 1/37 435/7.4 |
| 2016/0025626 A1 | 1/2016 | Dos Santos Fegadolli et al. |
| 2016/0069862 A1 | 3/2016 | Tucker et al. |
| 2016/0151466 A1 | 6/2016 | Dunning et al. |
| 2017/0097350 A1 | 4/2017 | Tucker et al. |
| 2018/0074044 A1 | 3/2018 | Piazza et al. |

FOREIGN PATENT DOCUMENTS

| | | |
|---|---|---|
| WO | 2006107921 | 10/2006 |
| WO | 2009035476 | 3/2009 |
| WO | 2010127400 | 11/2010 |
| WO | 2011047265 | 4/2011 |
| WO | 2012047325 | 4/2012 |
| WO | 2016025626 A2 | 2/2016 |

OTHER PUBLICATIONS

Sikorra S, Henke T, Swaminathan S, Galli T, Binz T. Identification of the amino acid residues rendering TI-VAMP insensitive toward botulinum neurotoxin B. J Mol Biol. Mar. 24, 2006;357(2):574-82. doi: 10.1016/j.jmb.2005.12.075. Epub Jan. 18, 2006. PMID: 16430921. (Year: 2006).*

Shone, C.C. and Roberts, A.K. (1994), Peptide Substrate Specificity and Properties of the zinc-endopeptidase Activity of Botulinum Type B Neurotoxin. European Journal of Biochemistry, 225: 263-270. https://doi.org/10.1111/j.1432-1033.1994.00263.x (Year: 1994).*

Kazuhide Yahata et al. Multi-gene Gateway clone design for expression of multiple heterologous genes in living cells: conditional gene expression at near physiological levels, Journal of Biotechnology, vol. 118, Issue 2, 2005, pp. 123-134, ISSN 0168-1656 (Year: 2005).*

Forbes J, Krishnamurthy K. Biochemistry, Peptide. [Updated Aug. 28, 2023]. In: StatPearls [Internet]. Treasure Island (FL): StatPearls Publishing; Jan. 2024—. Available from: https://www.ncbi.nlm.nih.gov/books/NBK562260/ (Year: 2024).*

Miyawaki et al., Fluorescent indicators for Ca2+ based on green fluorescent proteins and calmodulin, Letters to Nature, vol. 388, Aug. 1997, pp. 882-887.

Capkova et al., Investigations into Small Molecule Non-Peptidic Inhibitors of the Botulinum Neurotoxins, National Institutes of Health, Oct. 2009, vol. 54 (5), pp. 575-582.

Dong et al., Using fluorescent sensors to detect botulinum neurotoxin activity in vitro and in living cells, PNAS, Oct. 12, 2004, vol. 101, No. 41, pp. 14701-14706.

Fang et al., A yeast assay probes the interaction between botulinum neurotoxin serotype B and its SNARE substrate, PNAS, May 2, 2006, vol. 103, No. 18, pp. 6958-6963.

IPEA/US, International Preliminary Report on Patentability for International Application No. PCT/US10/52847, Nov. 11, 2011, 18 pages.

ISA/US, International Search Report and Written Opinion for International Application No. PCT/US10/52847, Feb. 22, 2011, 12 pages.

Joseph C. Larsen, U.S. Army Botulinum Neurotoxin (BoNT) Medical Therapeutics Research Program: Past Accomplishments and Future Directions, Drug Development Research, 2009, vol. 70, pp. 266-278.

Perpetuo et al., Enzymatic Profiling of Tetanus and Botulinum Neurotoxins Based on Vesicle-Associated-Membrane Protein Derived Fluorogenic Subtrates, Protein & Peptide Letters, 2008, vol. 15, pp. 1100-1106.

Pires-Alves et al., Tandem Fluorescent Proteins as Enhanced FRET-based Substrates for Botulinum Neurotoxin Activity, National Institutes of Health, Mar. 15, 2009, vol. 53 (4), pp. 392-399.

Siddiqui et al., Determinants of Synaptobrevin Regulation in Membranes, Molecular Biology of the Cell, Jun. 2007, vol. 18, pp. 2037-2046.

Sikorra et al., Substrate Recognition Mechanism of VAMP/Synaptobrevin-cleaving Clostridial Neurotoxins, The Journal of Biological Chemistry, Jul. 25, 2008, vol. 283, No. 30, pp. 21145-21152.

Kitzer, et al. Complement modulates the function of the ubiquitin-proteasome system and endoplasmic reticulum-associated degradation in glomerular epithelial cells, Mar. 1, 2012. Biochimica et Biophysica Acta. 10 pages.

Houser, et al. An improved short-lived fluorescent protein transcriptional reporter for S. cerevisiae. NIH Public Access, Dec. 2012. 19 pages.

Hackett, et al. A family of destabilized cyan fluorescent proteins as transcriptional reporters in S. cerevisiae. Yeast, 2006. 17 pages.

Reis, et al. The CRY box: a second APC(cdh1)-dependent degron in mammalian cdc20, EMBO Reports. Jul. 28, 2006. 6 pages.

Neefjes, et al. Fluorescent probes for protolysis: tools for drug discovery, www.nature.com, Jan. 2004. vol. 3. 12 pages.

Kota et al., 'A high content imaging assay for identification of Botulinum neurotoxin inhibitors', Journal of Visualized Experiments, vol. 93, Article No. 51915, pp. 1-10 (Nov. 2014).

Basavanna et al., 'Development of a cell-based functional assay for the detection of Clostridium botulinum neurotoxin types A and E', International Journal of Microbiology, vol. 2013, Article ID. 593219, pp. 1-7 (2013).

Dong et al., 'Using fluorescent sensors to detect botulinum neurotoxin activity in vitro and in living cells', PNAS, vol. 101, No. 41, pp. 14701-14706 (Oct. 12, 2004).

International Search Report International application No. PCT/US2017/032954 International filing date May 16, 2017.

European Search Report for European Patent Application No. 17800032.9, dated Sep. 20, 2023.

Jacques Neefies et al., "Flourescent Probes for Proteolysis: Tools for Drug Discovery", Drug Discovery, dated Jan. 2004, pp. 58-69, vol. 3.

Sequence Alignment of Seq ID No. 11 with AXS40811. Dated Dec. 24, 2009, 2 pages.

Sequence Alignment of Seq ID No. 12 with AAB41899. Dated Feb. 8, 2001, 2 pages.

Sequence Alignment of Seq ID No. 13 with AEQ21129. Dated May 3, 2007, 2 pages.

Sequence Alignment of Seq ID No. 14 with AYL83675. Dated Jan. 6, 2011, 3 pages.

Sequence Alignment of Seq ID No. 15 with BAN378839. Dated Jun. 6, 2013, 2 pages.

Sequence Alignment of Seq ID No. 16 with BDN17243. Dated Mar. 9, 2017, 2 pages.

Sequence Alignment of Seq ID No. 17 with AAM04299. Dated Oct. 9, 2001, 2 pages.

Sequence Alignment of Seq ID No. 18 with ABG73429. Dated May 1, 2003, 2 pages.

Sequence Alignment of Seq ID No. 19 with BCR43598 Dated Jul. 28, 2016, 2 pages.

* cited by examiner

```
  1         10        20        30        40        50        60        70
115        124       134       144       154       164       174       18
ATGGTGAGCAAGGGCGAGGAGCTGTTCACCGGGGTGGTGCCCATCCTGGTCGAGCTGGACGGCGACGTAA
                                                                    YFP 150       160       170       180       190       200       21
 264       274       284       294       304       314       32
CATCTGCACCACCGGCAAGCTGCCCGTGCCCTGGCCCACCCTCGTGACCACCTTCGGCTACGGCCTGCAG
                                                                    YFP 290       300       310       320       330       340       35
 404       414       424       434       444       454       46
TCCAGGAGCGCACCATCTTCTTCAAGGACGACGGCAACTACAAGACCCGCGCCGAGGTGAAGTTCGAGGG
                                                                    YFP 430       440       450       460       470       480       49
 544       554       564       574       584       594       60
AAGCTGGAGTACAACTACAACAGCCACAACGTCTATATCATGGCCGACAAGCAGAAGAACGGCATCAAGG
                                                                    YFP 570       580       590       600       610       620       63
 684       694       704       714       724       734       74
CCCCATCGGCGACGGCCCCGTGCTGCTGCCCGACAACCACTACCTGAGCTACCAGTCCGCCCTGAGCAAA
                                                                    YFP 710       720       730       740       750       760       77
 824       834       844       854       864       874       88
TGGACGAGCTGTACAAGAGTGGAGGCATGTCGGCTACCGCTGCCACCGTCCCGCCTGCCGCCCCGGCCGG
     YFP            Linker                 VAMP2

850       860       870       880       890       900       91
 964       974       984       994      1,004     1,014      1,0
GTGGATGAGGTGGTGGACATCATGAGGGTGAATGTGGACAAGGTCCTGGAGCGRGACCAGAAGCTATCGG
                                                                   VAMP2

990      1,000     1,010     1,020     1,030     1,040      1,0
1,104     1,114     1,124     1,134     1,144     1,154      1,1
GCGCAAATACTGGTGGAAAAACCTCAAGATGATGATCATCTTGGGAGTGATTTGCGCCATCATCCTCATC
                                                                   VAMP2
```

Plasmid pMD0032ORF encoding YFP-synaptobrevin (VAMP2) SEQ ID NO. 1
(continued on FIG. 6B)

*FIG. 6A*

```
  0         80        90       100       110       120       130       140
 84        194       204       214       224       234       244       254
AACGGCCACAAGTTCAGCGTGTCCGGCGAGGGCGAGGGCGATGCCACCTACGGCAAGCTGACCCTGAAGTT
                                    YFP 10        220       230       240       250       260       270       280
 24        334       344       354       364       374       384       394
GTGCTTCGCCCGCTACCCCGACCACATGAAGCAGCACGACTTCTTCAAGTCCGCCATGCCCGAAGGCTACG
                                    YFP 50        360       370       380       390       400       410       420
 64        474       484       494       504       514       524       534
GCGACACCCTGGTGAACCGCATCGAGCTGAAGGGCATCGACTTCAAGGAGGACGGCAACATCCTGGGGCAC
                                    YFP 90        500       510       520       530       540       550       560
 04        614       624       634       644       654       664       674
GTGAACTTCAAGATCCGCCACAACATCGAGGACGGCAGCGTGCAGCTCGCCGACCACTACCAGCAGAACAC
                                    YFP 30        640       650       660       670       680       690       700
 44        754       764       774       784       794       804       814
AGACCCCAACGAGAAGCGCGATCACATGGTCCTGCTGGAGTTCGTGACCGCCGCCGGGATCACTCTCGGCA
                                    YFP 70        780       790       800       810       820       830       840
 84        894       904       914       924       934       944       954
GCGAGGGTGGCCCCCCTGCACCTCCTCCAAATCTTACCAGTAACAGGAGACTGCAGCAGACCCAGGCCCAG
                                   VAMP2

10        920       930       940       950       960       970       980
024       1,034     1,044     1,054     1,064     1,074     1,084     1,094
GAACTGGATGATCGCGCAGATGCCCTCCAGGCAGGGGCCTCCCAGTTTGAAACAAGTGCAGCCAAGCTCAA
                                   VAMP2

050      1,060     1,070    1,077
 64      1,174     1,184    1,191
CATCATCATCGTTTACTTCAGCACTTAA
```

Plasmid pMD0032ORF encoding YFP-synaptobrevin (VAMP2) SEQ ID NO. 1
(continued from FIG. 6A)

*FIG. 6B*

```
  1         10         20         30         40         50         60         70
118        127        137        147        157        167        177        18
ATGGTGAGCAAGGGCGAGGAGCTGTTCACCGGGGTGGTGCCCATCCTGGTCGAGCTGGACGGCGACGTAA
                                      ECFP 150        160        170        180        190        200        21
           267        277        287        297        307        317        32
CATCTGCACCACCGGCAAGCTGCCCGTGCCCTGGCCCACCCTCGTGACCACCCTGACCTGGGGCGTGCAG
                                      ECFP 290        300        310        320        330        340        35
           407        417        427        437        447        457        46
TCCAGGAGCGCACCATCTTCTTCAAGGACGACGGCAACTACAAGACCCGCGCCGAGGTGAAGTTCGAGGG
                                      ECFP 430        440        450        460        470        480        49
           547        557        567        577        587        597        60
AAGCTGGAGTACAACTACATCAGCCACAACGTCTATATCACCGCCGACAAGCAGAAGAACGGCATCAAGG
                                      ECFP 570        580        590        600        610        620        63
           687        697        707        717        727        737        74
CCCCATCGGCGACGGCCCCGTGCTGCTGCCCGACAACCACTACCTGAGCACCCAGTCCGCCCTGAGCAAA
                                      ECFP 710        720        730        740        750        760        77
           827        837        847        857        867        877        88
TGGACGAGCTGTACAAGAGTGGAGGCATGTCGGCTACCGCTGCCACCGTCCCGCCTGCCGCCCCGGCCGG
      ECFP      Linker                      VAMP2

850        860        870        880        890        900        91
           967        977        987        997       1,007      1,017       1,0
GTGGATGAGGTGGTGGACATCATGAGGGTGAATGTGGACAAGGTCCTGGAGCGRGACCAGAAGCTATCGG
                                      VAMP2

990       1,000      1,010      1,020      1,030      1,040       1,0
          1,107      1,117      1,127      1,137      1,147      1,157       1,1
GCGCAAATACTGGTGGAAAAACCTCAAGATGATGATCATCTTGGGAGTGATTTGCGCCATCATCCTCATC
                                      VAMP2
```

Plasmid pMD0034ORF encoding CFP-synaptobrevin (VAMP2) SEQ ID NO. 2 (continued on FIG. 7B)

*FIG. 7A*

```
  0       80        90        100       110       120       130       140
  |        |         |         |         |         |         |         |
  7       197       207       217       227       237       247       257
  ACGGCCACAAGTTCAGCGTGTCCGGCGAGGGCGAGGGCGATGCCACCTACGGCAAGCTGACCCTGAAGTT
                                    ECFP 0       220       230       240       250       260       270       280
  |        |         |         |         |         |         |         |
  7       337       347       357       367       377       387       397
  TGCTTCAGCCGCTACCCCGACCACATGAAGCAGCACGACTTCTTCAAGTCCGCCATGCCCGAAGGCTACG
                                    ECFP 0       360       370       380       390       400       410       420
  |        |         |         |         |         |         |         |
  7       477       487       497       507       517       527       537
  CGACACCCTGGTGAACCGCATCGAGCTGAAGGGCATCGACTTCAAGGAGGACGGCAACATCCTGGGGCAC
                                    ECFP 0       500       510       520       530       540       550       560
  |        |         |         |         |         |         |         |
  7       617       627       637       647       657       667       677
  CCAACTTCAAGATCCGCCACAACATCGAGGACGGCAGCGTGCAGCTCGCCGACCACTACCAGCAGAACAC
                                    ECFP 0       640       650       660       670       680       690       700
  |        |         |         |         |         |         |         |
  7       757       767       777       787       797       807       817
  GACCCCAACGAGAAGCGCGATCACATGGTCCTGCTGGAGTTCGTGACCGCCGCCGGGATCACTCTCGGCA
                                    ECFP 0       780       790       800       810       820       830       840
  |        |         |         |         |         |         |         |
  7       897       907       917       927       937       947       957
  CGAGGGTGGCCCCCCTGCACCTCCTCCAAATCTTACCAGTAACAGGAGACTGCAGCAGACCCAGGCCCAG
                                    VAMP2

0       920       930       940       950       960       970       980
  |        |         |         |         |         |         |         |
  27     1,037     1,047     1,057     1,067     1,077     1,087     1,097
  AACTGGATGATCGCGCAGATGCCCTCCAGGCAGGGGCCTCCCAGTTTGAAACAAGTGCAGCCAAGCTCAA
                                    VAMP2

50     1,060     1,070     1,077
  |        |         |         |
  67     1,177     1,187     1,194
  ATCATCATCGTTTACTTCAGCACTTAA
                VAMP2
```

Plasmid pMD0034ORF encoding CFP-synaptobrevin (VAMP2) SEQ ID NO. 2 (continued from FIG. 7A)

FIG. 7B

```
  1        10        20        30        40        50        60        70
124       133       143       153       163       173       183       19
ATGGTGAGCAAGGGCGAGGAGCTGTTCACCGGGGTGGTGCCCATCCTGGTCGAGCTGGACGGCGACGTAA
                                    YFP 150       160       170       180       190       200       21
273       283       293       303       313       323       33
CATCTGCACCACCGGCAAGCTGCCCGTGCCCTGGCCCACCCTCGTGACCACCTTCGGCTACGGCCTGCAG
                                    YFP 290       300       310       320       330       340       35
413       423       433       443       453       463       47
TCCAGGAGCGCACCATCTTCTTCAAGGACGACGGCAACTACAAGACCCGCGCCGAGGTGAAGTTCGAGGG
                                    YFP 430       440       450       460       470       480       49
553       563       573       583       593       603       61
AAGCTGGAGTACAACTACAACAGCCACAACGTCTATATCATGGCCGACAAGCAGAAGAACGGCATCAAGG
                                    YFP 570       580       590       600       610       620       63
693       703       713       723       733       743       75
CCCCATCGGCGACGGCCCCGTGCTGCTGCCCGACAACCACTACCTGAGCTACCAGTCCGCCCTGAGCAAA
                                    YFP 710       720       730       740       750       760       77
833       843       853       863       873       883       89
TGGACGAGCTGTACAAGAGTGGAGGCATGTCGGCTACCGCTGCCACCGTCCCGCCTGCCGCCCCGGCCGG
       YFP          Linker                      VAMP2

850       860       870       880       890       900       91
973       983       993      1,003     1,013     1,023     1,03
GTGGATGAGGTGGTGGACATCATGAGGGTGAATGTGGACAAGGTCCTGGAGCGRGACCAGAAGCTATCGG
                                   VAMP2

990      1,000     1,010     1,020     1,030     1,040     1,05
1,113     1,123     1,133     1,143     1,153     1,163     1,1
GCGCAAATACTGGTGGAAAAACCTCAAGATGATGATCATCTTGGGAGTGATTTGCGCCATCATCCTCATC
                                   VAMP2
```

Plasmid pMD0034ORF encoding YFP-synaptobrevin (VAMP2) SEQ ID NO. 3 (continued on FIG. 8B)

FIG. 8A

```
  0         80         90        100        110        120        130        140
  |          |          |          |          |          |          |          |
 93        203        213        223        233        243        253        263
AACGGCCACAAGTTCAGCGTGTCCGGCGAGGGCGAGGGCGATGCCACCTACGGCAAGCTGACCCTGAAGTT
                                        YFP 10        220        230        240        250        260        270        280
  |          |          |          |          |          |          |          |
 33        343        353        363        373        383        393        403
GTGCTTCGCCCGCTACCCCGACCACATGAAGCAGCACGACTTCTTCAAGTCCGCCATGCCCGAAGGCTACG
                                        YFP 50        360        370        380        390        400        410        420
  |          |          |          |          |          |          |          |
 73        483        493        503        513        523        533        543
GCGACACCCTGGTGAACCGCATCGAGCTGAAGGGCATCGACTTCAAGGAGGACGGCAACATCCTGGGGCAC
                                        YFP 90        500        510        520        530        540        550        560
  |          |          |          |          |          |          |          |
 13        623        633        643        653        663        673        683
GTGAACTTCAAGATCCGCCACAACATCGAGGACGGCAGCGTGCAGCTCGCCGACCACTACCAGCAGAACAC
                                        YFP 30        640        650        660        670        680        690        700
  |          |          |          |          |          |          |          |
 53        763        773        783        793        803        813        823
AGACCCCAACGAGAAGCGCGATCACATGGTCCTGCTGGAGTTCGTGACCGCCGCCGGGATCACTCTCGGCA
                                        YFP 70        780        790        800        810        820        830        840
  |          |          |          |          |          |          |          |
 93        903        913        923        933        943        953        963
GCGAGGGTGGCCCCCCTGCACCTCCTCCAAATCTTACCAGTAACAGGAGACTGCAGCAGACCCAGGCCCAG
                                       VAMP2

10        920        930        940        950        960        970        980
  |          |          |          |          |          |          |          |
033      1,043      1,053      1,063      1,073      1,083      1,093      1,103
GAACTGGATGATCGCGCAGATGCCCTCCAGGCAGGGGCCTCCCAGTTTGAAACAAGTGCAGCCAAGCTCAA
                                       VAMP2

50      1,060      1,070      1,077
  |          |          |          |
 73      1,183      1,193      1,200
CATCATCATCGTTTACTTCAGCACTTAA
              VAMP2
```

Plasmid pMD0034ORF encoding YFP-synaptobrevin (VAMP2) SEQ ID NO. 3 (continued from FIG. 8A)

FIG. 8B

```
  1        10        20        30        40        50        60        70
ATGGTGAGCAAGGGCGAGGAGCTGTTCACCGGGGTGGTGCCCATCCTGGTCGAGCTGGACGGCGACGTAA
{                                    ECFP 150       160       170       180       190       200       21
CATCTGCACCACCGGCAAGCTGCCCGTGCCCCTGGCCCACCCTCGTGACCACCCTGACCTGGGGCGTGCAG
{                                    ECFP 290       300       310       320       330       340       35
TCCAGGAGCGCACCATCTTCTTCAAGGACGACGGCAACTACAAGACCCGCGCCGAGGTGAAGTTCGAGGG
{                                    ECFP 430       440       450       460       470       480       49
AAGCTGGAGTACAACTACATCAGCCACAACGTCTATATCACCGCCGACAAGCAGAAGAACGGCATCAAGG
{                                    ECFP 570       580       590       600       610       620       63
CCCCATCGGCGACGGCCCCGTGCTGCTGCCCGACAACCACTACCTGAGCACCCAGTCCGCCCTGAGCAAA
{                                    ECFP 710       720       730       740       750       760       77
TGGACGAGCTGTACAAGAGTGGAGGCATGTCGGCTACCGCTGCCACCGTCCCGCCTGCCGCCCCGGCCGG
{      ECFP      }{  Linker  }{                VAMP2

850       860       870       880       890       900       91
GTGGATGAGGTGGTGGACATCATGAGGGTGAATGTGGACAAGGTCCTGGAGCGRGACCAGAAGCTATCGG
{                                    VAMP2

990      1,000     1,010     1,020     1,030     1,040      1,0
GCGCAAATACTGGTGGAAAAACCTCAAGATGATGATCATCTTGGGAGTGATTTGCGCCATCATCCTCATC
{                                    VAMP2
```

Plasmid pMD0071ORF encoding CFP-synaptobrevin (VAMP2) SEQ ID NO. 4 (continued on FIG. 9B)

*FIG. 9A*

```
        0             80            90           100           110           120           130           140
        |             |             |            |             |             |             |             |
AACGGCCACAAGTTCAGCGTGTCCGGCGAGGGCGAGGGCGATGCCACCTACGGCAAGCTGACCCTGAAGTT
                                          ECFP
```

```
       10            220           230           240           250           260           270           280
        |             |             |             |             |             |             |             |
GTGCTTCAGCCGCTACCCCGACCACATGAAGCAGCACGACTTCTTCAAGTCCGCCATGCCCGAAGGCTACG
                                          ECFP
```

```
       50            360           370           380           390           400           410           420
        |             |             |             |             |             |             |             |
GCGACACCCTGGTGAACCGCATCGAGCTGAAGGGCATCGACTTCAAGGAGGACGGCAACATCCTGGGGCAC
                                          ECFP
```

```
       90            500           510           520           530           540           550           560
        |             |             |             |             |             |             |             |
GCCAACTTCAAGATCCGCCACAACATCGAGGACGGCAGCGTGCAGCTCGCCGACCACTACCAGCAGAACAC
                                          ECFP
```

```
       30            640           650           660           670           680           690           700
        |             |             |             |             |             |             |             |
AGACCCCAACGAGAAGCGCGATCACATGGTCCTGCTGGAGTTCGTGACCGCCGCCGGGATCACTCTCGGCA
                                          ECFP
```

```
       70            780           790           800           810           820           830           840
        |             |             |             |             |             |             |             |
GCGAGGGTGGCCCCCCTGCACCTCCTCCAAATCTTACCAGTAACAGGAGACTGCAGCAGACCCAGGCCCAG
                                          VAMP2
```

```
       10            920           930           940           950           960           970           980
        |             |             |             |             |             |             |             |
GAACTGGATGATCGCGCAGATGCCCTCCAGGCAGGGGCCTCCGTGTTTGAAACAAGTGCAGCCAAGCTCAA
                                          VAMP2
```

```
      050          1,060          1,070         1,077
        |             |             |            |
CATCATCATCGTTTACTTCAGCACTTAA
                 VAMP2
```

Plasmid pMD0071ORF encoding CFP-synaptobrevin (VAMP2) SEQ ID NO. 4
(continued from FIG. 9A)

FIG. 9B

```
  1         10        20        30        40        50        60        70
124        133       143       153       163       173       183        19
ATGGTGAGCAAGGGCGAGGAGCTGTTCACCGGGGTGGTGCCCATCCTGGTCGAGCTGGACGGCGACGTAA
(                                                                    YFP 150       160       170       180       190       200        21
          273       283       293       303       313       323        33
CATCTGCACCACCGGCAAGCTGCCCGTGCCCCTGGCCCACCCTCGTGACCACCTTCGGCTACGGCCTGCAG
                                                                     YFP 290       300       310       320       330       340        35
          413       423       433       443       453       463        47
TCCAGGAGCGCACCATCTTCTTCAAGGACGACGGCAACTACAAGACCCGCGCCGAGGTGAAGTTCGAGGG
                                                                     YFP 430       440       450       460       470       480        49
          553       563       573       583       593       603        61
AAGCTGGAGTACAACTACAACAGCCACAACGTCTATATCATGGCCGACAAGCAGAAGAACGGCATCAAGG
                                                                     YFP 570       580       590       600       610       620        63
          693       703       713       723       733       743        75
CCCCATCGGCGACGGCCCCGTGCTGCTGCCCGACAACCACTACCTGAGCTACCAGTCCGCCCTGAGCAAA
                                                                     YFP 710       720       730       740       750       760        77
          833       843       853       863       873       883        89
TGGACGAGCTGTACAAGAGTGGAGGCATGTCGGCTACCGCTGCCACCGTCCCGCCTGCCGCCCCGGCCGG
( YFP    )( Linker )(                    VAMP2

850       860       870       880       890       900        91
          973       983       993     1,003     1,013     1,023       1,0
GTGGATGAGGTGGTGGACATCATGAGGGTGAATGTGGACAAGGTCCTGGAGCGRGACCAGAAGCTATCGG
                                                                    VAMP2

990     1,000     1,010     1,020     1,030     1,040       1,0
         1,113   1,123     1,133     1,143     1,153     1,163        1,1
GCGCAAATACTGGTGGAAAAACCTCAAGATGATGATCATCTTGGGAGTGATTTGCGCCATCATCCTCATC
                                                                    VAMP2
```

Plasmid pMD0071ORF encoding YFP-synaptobrevin (VAMP2) SEQ ID NO. 5
(continued on FIG. 10B)

*FIG. 10A*

```
  0        80         90        100        110        120        130        140
 93       203        213        223        233        243        253        263
AACGGCCACAAGTTCAGCGTGTCCGGCGAGGGCGAGGGCGATGCCACCTACGGCAAGCTGACCCTGAAGTT
         YFP 10       220        230        240        250        260        270        280
 33       343        353        363        373        383        393        403
GTGCTTCGCCCGCTACCCCGACCACATGAAGCAGCACGACTTCTTCAAGTCCGCCATGCCCGAAGGCTACG
         YFP 50       360        370        380        390        400        410        420
 73       483        493        503        513        523        533        543
GCGACACCCTGGTGAACCGCATCGAGCTGAAGGGCATCGACTTCAAGGAGGACGGCAACATCCTGGGGCAC
         YFP 90       500        510        520        530        540        550        560
 13       623        633        643        653        663        673        683
GTGAACTTCAAGATCCGCCACAACATCGAGGACGGCAGCGTGCAGCTCGCCGACCACTACCAGCAGAACAC
         YFP 30       640        650        660        670        680        690        700
 53       763        773        783        793        803        813        823
AGACCCCAACGAGAAGCGCGATCACATGGTCCTGCTGGAGTTCGTGACCGCCGCCGGGATCACTCTCGGCA
         YFP 70       780        790        800        810        820        830        840
 93       903        913        923        933        943        953        963
GCGAGGGTGGCCCCCCTGCACCTCCTCCAAATCTTACCAGTAACAGGAGACTGCAGCAGACCCAGGCCCAG
              VAMP2

10       920        930        940        950        960        970        980
033      1,043      1,053      1,063      1,073      1,083      1,093      1,103
GAACTGGATGATCGCGCAGATGCCCTCCAGGCAGGGGCCTCCCAGTTTGAAACAAGTGCAGCCAAGCTCAA
              VAMP2

050      1,060      1,070      1,077
 73      1,183      1,193      1,200
CATCATCATCGTTTACTTCAGCACTTAA
              VAMP2
```

Plasmid pMD0071ORF encoding YFP-synaptobrevin (VAMP2) SEQ ID NO. 5 (continued from FIG. 10A)

*FIG. 10B*

```
  1         10        20        30        40        50        60        70
133        142       152       162       172       182       192        20
ATGGTGAGCAAGGGCGAGGAGCTGTTCACCGGGGTGGTGCCCATCCTGGTCGAGCTGGACGGCGACGTAA
[                                                                    YFP
          150       160       170       180       190       200        21
          282       292       302       312       322       332        34
CATCTGCACCACCGGCAAGCTGCCCGTGCCCTGGCCCACCCTCGTGACCACCTTCGGCTACGGCCTGCAG
                                                                     YFP
          290       300       310       320       330       340        35
          422       432       442       452       462       472        48
TCCAGGAGCGCACCATCTTCTTCAAGGACGACGGCAACTACAAGACCCGCGCCGAGGTGAAGTTCGAGGG
                                                                     YFP
          430       440       450       460       470       480        49
          562       572       582       592       602       612        62
AAGCTGGAGTACAACTACAACAGCCACAACGTCTATATCATGGCCGACAAGCAGAAGAACGGCATCAAGG
                                                                     YFP
          570       580       590       600       610       620        63
          702       712       722       732       742       752        76
CCCCATCGGCGACGGCCCCGTGCTGCTGCCCGACAACCACTACCTGAGCTACCAGTCCGCCCTGAGCAAA
                                                                     YFP
          710       720       730       740       750       760        77
          842       852       862       872       882       892        90
TGGACGAGCTGTACAAGTCTGGAGGCAAGCTTGCAATGGTGAGCAAGGGCGAGGAGCTGTTCACCGGGGT
[    YFP    ][       Linker       ][                YFP
          850       860       870       880       890       900        91
          982       992      1,002     1,012     1,022     1,032      1,04
GGCGATGCCACCTACGGCAAGCTGACCCTGAAGTTCATCTGCACCACCGGCAAGCTGCCCGTGCCCTGGC
                                                                     YFP
          990      1,000     1,010     1,020     1,030     1,040      1,0
         1,122     1,132     1,142     1,152     1,162     1,172      1,1
CGACTTCTTCAAGTCCGCCATGCCCGAAGGCTACGTCCAGGAGCGCACCATCTTCTTCAAGGACGACGGC
                                                                     YFP
         1,130     1,140     1,150     1,160     1,170     1,180      1,1
         1,262     1,272     1,282     1,292     1,302     1,312      1,3
TCGACTTCAAGGAGGACGGCAACATCCTGGGGCACAAGCTGGAGTACAACTACAACAGCCACAACGTCTA
                                                                     YFP
``` pMD0183ORF encoding YFP-YFP-synaptobrevin (VAMP2) SEQ ID NO. 8
(continued on FIG. 11B)

*FIG. 11A*

```
     80      90     100     110     120     130     140
    212     222     232     242     252     262     272
ACGGCCACAAGTTCAGCGTGTCCGGCGAGGGCGAGGGCGATGCCACCTACGGCAAGCTGACCCTGAAGTT
                                   YFP 220     230     240     250     260     270     280
    352     362     372     382     392     402     412
TGCTTCGCCCGCTACCCCGACCACATGAAGCAGCACGACTTCTTCAAGTCCGCCATGCCCGAAGGCTACG
                                   YFP 360     370     380     390     400     410     420
    492     502     512     522     532     542     552
CGACACCCTGGTGAACCGCATCGAGCTGAAGGGCATCGACTTCAAGGAGGACGGCAACATCCTGGGGCAC
                                   YFP 500     510     520     530     540     550     560
    632     642     652     662     672     682     692
TGAACTTCAAGATCCGCCACAACATCGAGGACGGCAGCGTGCAGCTCGCCGACCACTACCAGCAGAACAC
                                   YFP 640     650     660     670     680     690     700
    772     782     792     802     812     822     832
GACCCCAACGAGAAGCGCGATCACATGGTCCTGCTGGAGTTCGTGACCGCCGCCGGGATCACTCTCGGCA
                                   YFP 780     790     800     810     820     830     840
    912     922     932     942     952     962     972
GGTGCCCATCCTGGTCGAGCTGGACGGCGACGTAAACGGCCACAAGTTCAGCGTGTCCGGCGAGGGCGAG
                                   YFP 920     930     940     950     960     970     980
  1,052   1,062   1,072   1,082   1,092   1,102   1,112
CCACCCTCGTGACCACCTTCGGCTACGGCCTGCAGTGCTTCGCCCGCTACCCCGACCACATGAAGCAGCA
                                   YFP 1,060   1,070   1,080   1,090   1,100   1,110   1,120
   1,192   1,202   1,212   1,222   1,232   1,242   1,252
AACTACAAGACCCGCGCCGAGGTGAAGTTCGAGGGCGACACCCTGGTGAACCGCATCGAGCTGAAGGGCA
                                   YFP 1,200   1,210   1,220   1,230   1,240   1,250   1,260
   1,332   1,342   1,352   1,362   1,372   1,382   1,392
TATCATGGCCGACAAGCAGAAGAACGGCATCAAGGTGAACTTCAAGATCCGCCACAACATCGAGGACGGC
                                   YFP
``` pMD0183ORF encoding YFP-YFP-synaptobrevin (VAMP2) SEQ ID NO. 8
(continued from 11A and continued on FIG. 11C)

*FIG. 11B*

```
     1,270      1,280      1,290      1,300      1,310      1,320      1,3
     1,402      1,412      1,422      1,432      1,442      1,452      1,4
AGCGTGCAGCTCGCCGACCACTACCAGCAGAACACCCCCATCGGCGACGGCCCCGTGCTGCTGCCCGACA
                                    YFP 1,410      1,420      1,430      1,440      1,450      1,460      1,4
     1,542      1,552      1,562      1,572      1,582      1,460      1,4
GGAGTTCGTGACCGCCGCCGGGATCACTCTCGGCATGGACGAGCTGTACAAGAGTGGAGGCATGTCGGCT
                            YFP                          Linker    VAMP2

1,550      1,560      1,570      1,580      1,590      1,600      1,6
     1,550      1,560      1,570      1,580      1,590      1,600      1,6
CCAGTAACAGGAGACTGCAGCAGACCCAGGCCCAGGTGGATGAGGTGGTGGACATCATGAGGGTGAATGT
                                   VAMP2

1,690      1,700      1,710      1,720      1,730      1,740      1,7
     1,690      1,700      1,710      1,720      1,730      1,740      1,7
GCCTCCCAGTTTGAAACAAGTGCAGCCAAGCTCAAGCGCAAATACTGGTGGAAAAACCTCAAGATGATGA
                                   VAMP2
``` pMD0183ORF encoding YFP-YFP-synaptobrevin (VAMP2) SEQ ID NO. 8
(continued from 11B and continued on FIG. 11D)

*FIG. 11C*

```
30      1,340     1,350     1,360     1,370     1,380     1,390     1,400
62      1,472     1,482     1,492     1,502     1,512     1,522     1,532
ACCACTACCTGAGCTACCAGTCCGCCCTGAGCAAAGACCCCAACGAGAAGCGCGATCACATGGTCCTGCT
                                    YFP 70      1,480     1,490     1,500     1,510     1,520     1,530     1,540
70      1,480     1,490     1,500     1,510     1,520     1,530     1,540
ACCGCTGCCACCGTCCCGCCTGCCGCCCCGGCCGGCGAGGGTGGCCCCCCTGCACCTCCTCCAAATCTTA
                                   VAMP2

10      1,620     1,630     1,640     1,650     1,660     1,670     1,680
10      1,620     1,630     1,640     1,650     1,660     1,670     1,680
GGACAAGGTCCTGGAGCGRGACCAGAAGCTATCGGAACTGGATGATCGCGCAGATGCCCTCCAGGCAGGG
                                   VAMP2

50      1,760     1,770     1,780     1,790     1,800     1,812
50      1,760     1,770     1,780     1,790     1,800     1,812
TCATCTTGGGAGTGATTTGCGCCATCATCCTCATCATCATCGTTTACTTCAGCACTTAA
                                   VAMP2
``` pMD0183ORF encoding YFP-YFP-synaptobrevin (VAMP2) SEQ ID NO. 8 (continued from FIG. 11C)

FIG. 11D

```
  1         10        20        30        40        50        60        70
ATGGTGAGCAAGGGCGAGGAGCTGTTCACCGGGGTGGTGCCCATCCTGGTCGAGCTGGACGGCGACGTAA
                                        ECFP 150       160       170       180       190       200       21
CATCTGCACCACCGGCAAGCTGCCCGTGCCCTGGCCCACCCTCGTGACCACCCTGACCTGGGGCGTGCAG
                                        ECFP 290       300       310       320       330       340       35
TCCAGGAGCGCACCATCTTCTTCAAGGACGACGGCAACTACAAGACCCGCGCCGAGGTGAAGTTCGAGGG
                                        ECFP                          EC 430       440       450       460       470       480       49
AAGCTGGAGTACAACTACATCAGCCACAACGTCTATATCACCGCCGACAAGCAGAAGAACGGCATCAAGG
                                        ECFP 570       580       590       600       610       620       63
CCCCATCGGCGACGGCCCCGTGCTGCTGCCCGACAACCACTACCTGAGCACCCAGTCCGCCCTGAGCAAA
                                        ECFP 710       720       730       740       750       760       77
TGGACGAGCTGTACAAGAGTGGAGGCATGTCGGCTACCGCTGCCACCGTCCCGCCTGCCGCCCCGGCCGG
     ECFP          Linker                    VAMP2

850       860       870       880       890       900       91
GTGGATGAGGTGGTGGACATCATGAGGGTGAATGTGGACAAGGTCCTGGAGCGRGACCAGAAGCTATCGG
                                        VAMP2

990      1,000     1,010     1,020     1,030     1,040      1,0
GCGCAAATACTGGTGGAAAAACCTCAAGATGATGATCATCTTGGGAGTGATTTGCGCCATCATCCTCATC
                                        VAMP2
```

Plasmid pMD0185ORF encoding CFP-synaptobrevin (VAMP2) SEQ ID NO. 6 (continued on FIG. 12B)

*FIG. 12A*

```
   0        80         90        100        110        120        130        140
   |         |          |          |          |          |          |          |
ACGGCCACAAGTTCAGCGTGTCCGGCGAGGGCGAGGGCGATGCCACCTACGGCAAGCTGACCCTGAAGTT
          ECFP 0       220        230        240        250        260        270        280
   |         |          |          |          |          |          |          |
TGCTTCAGCCGCTACCCCGACCACATGAAGCAGCACGACTTCTTCAAGTCCGCCATGCCCGAAGGCTACG
          ECFP 0       360        370        380        390        400        410        420
   |         |          |          |          |          |          |          |
CGACACCCTGGTGAACCGCATCGAGCTGAAGGGCATCGACTTCAAGGAGGACGGCAACATCCTGGGGCAC
          ECFP 0       500        510        520        530        540        550        560
   |         |          |          |          |          |          |          |
CCAACTTCAAGATCCGCCACAACATCGAGGACGGCAGCGTGCAGCTCGCCGACCACTACCAGCAGAACAC
          ECFP 0       640        650        660        670        680        690        700
   |         |          |          |          |          |          |          |
GACCCCAACGAGAAGCGCGATCACATGGTCCTGCTGGAGTTCGTGACCGCCGCCGGGATCACTCTCGGCA
          ECFP 0       780        790        800        810        820        830        840
   |         |          |          |          |          |          |          |
CGAGGGTGGCCCCCCTGCACCTCCTCCAAATCTTACCAGTAACAGGAGACTGCAGCAGACCCAGGCCCAG
          VAMP2

0       920        930        940        950        960        970        980
   |         |          |          |          |          |          |          |
AACTGAATAATCGCGCAAATGCCCTCCAGGCAGGGGCCTCCGTGTTTGAAACAAGTGCAGCCAAGCTCAA
          VAMP2

50      1,060      1,070     1,077
   |         |          |          |
ATCATCATCGTTTACTTCAGCACTTAA
          VAMP2
```

Plasmid pMD0185ORF encoding CFP-synaptobrevin (VAMP2) SEQ ID NO. 6
(continued from FIG. 12A)

FIG. 12B

```
  1         10        20        30        40        50        60        7
367        376       386       396       406       416       426       43
ATGAAGCAGCACGACTTCTTCAAGTCCGCCATGCCCGAAGGCTACGTCCAGGAGCGCACCATCTTCTTCA
                                    YFP 150       160       170       180       190       200        21
 516       526       536       546       556       566        57
GCTGAAGGGCATCGACTTCAAGGAGGACGGCAACATCCTGGGGCACAAGCTGGAGTACAACTACAACAGC
                                    YFP 290       300       310       320       330       340        35
 656       666       676       686       696       706        71
TCGAGGACGGCAGCGTGCAGCTCGCCGACCACTACCAGCAGAACACCCCCATCGGCGACGGCCCCGTGCT
                                    YFP 430       440       450       460       470       480        49
 796       806       816       826       836       846        85
ATGGTCCTGCTGGAGTTCGTGACCGCCGCCGGGATCACTCTCGGCATGGACGAGCTGTACAAGAGTGGAG
                                    YFP                          Linker 570       580       590       600       610       620        63
 936       946       956       966       976       986        99
TCCAAATCTTACCAGTAACAGGAGACTGCAGCAGACCCAGGCCCAGGTGGATGAGGTGGTGGACATCATG
                                    VAMP2

710       720       730       740       750       760        77
1,076     1,086     1,096     1,106     1,116     1,126      1,13
TCCAGGCAGGGGCCTCCCAGTTTGAAACAAGTGCAGCCAAGCTCAAGCGCAAATACTGGTGGAAAAACCT
                                    VAMP2

843
1,209
TAA
    VAMP2
```

Plasmid pMD0185ORF encoding YFP-synaptobrevin (VAMP2) SEQ ID NO. 7
(continued on FIG. 13B)

*FIG. 13A*

```
    0         80          90         100         110         120         130         140
    |         |           |          |           |           |           |           |
   36        446         456        466         476         486         496         506
AAGGACGACGGCAACTACAAGACCCGCGCCGAGGTGAAGTTCGAGGGCGACACCCTGGTGAACCGCATCGA
                                          YFP 10        220         230        240         250         260         270         280
    |         |           |          |           |           |           |           |
   76        586         596        606         616         626         636         646
CCACAACGTCTATATCATGGCCGACAAGCAGAAGAACGGCATCAAGGTGAACTTCAAGATCCGCCACAACA
                                          YFP 50        360         370        380         390         400         410         420
    |         |           |          |           |           |           |           |
   16        726         736        746         756         766         776         786
TGCTGCCCGACAACCACTACCTGAGCTACCAGTCCGCCCTGAGCAAAGACCCCAACGAGAAGCGCGATCAC
                                          YFP 90        500         510        520         530         540         550         560
    |         |           |          |           |           |           |           |
   56        866         876        886         896         906         916         926
GGCATGTCGGCTACCGCTGCCACCGTCCCGCCTGCCGCCCCGGCCGGCGAGGGTGGCCCCCCTGCACCTCC
                                       >    VAMP2

30        640         650        660         670         680         690         700
    |         |           |          |           |           |           |           |
   96       1,006       1,016      1,026       1,036       1,046       1,056       1,066
GAGGGTGAATGTGGACAAGGTCCTGGAGCGRGACCAGAAGCTATCGGAACTGGATGATCGCGCAGATGCCC
                                         VAMP2

70        780         790        800         810         820         830         840
    |         |           |          |           |           |           |           |
   36       1,146       1,156      1,166       1,176       1,186       1,196       1,206
TCAAGATGATGATCATCTTGGGAGTGATTTGCGCCATCATCCTCATCATCATCATCGTTTACTTCAGCACT
                                         VAMP2
```

Plasmid pMD0185ORF encoding YFP-synaptobrevin (VAMP2) SEQ ID NO. 7 (continued from FIG. 13A)

REPORTING CONSTRUCT WITH SYNAPTOBREVIN BASED MOIETY

This application is a divisional application of U.S. patent application Ser. No. 15/597,002, filed May 16, 2017, which claims the benefit of U.S. Provisional Application No. 62/404,513, filed on Oct. 5, 2016, and U.S. Provisional Application No. 62/336,964, filed May 16, 2016. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is characterization of botulinum neurotoxins using cell based assays, particularly botulinum serotype B neurotoxin.

BACKGROUND

The following description includes information that may be useful in understanding the present invention. It is not an admission that any of the information provided herein is prior art or relevant to the presently claimed invention, or that any publication specifically or implicitly referenced is prior art.

Botulinum neurotoxins (BoNTs) are extremely toxic proteins and can be classified into distinct subgroups based, inter alia, on peptide sequence and/or substrate specificity. All of the naturally occurring BoNTs (BoNT/A-G) are composed of a heavy chain that mediates toxin entry into a target cell and a light chain with zinc-dependent protease activity that hydrolyzes selected SNARE proteins that mediate fusion of neurotransmitter vesicles to the membrane that forms part of the synaptic cleft.

For example, the light chain of BoNT/A hydrolyzes with high specificity SNAP-25, which is required for vesicle-mediated exocytosis of acetylcholine into the synaptic cleft. Known assays for such hydrolytic activity include those described in PCT Application Publication No. WO 2009/035476, to Fish and Dong, which describes the use of a peptide construct that includes a fluorophore and a quencher that are covalently linked to the respective ends of a SNAP-25 sequence. All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply. Cleavage by BoNT/A (or other BoNTs with a substrate specificity towards SNAP-25) result in physical separation of the cleavage products and so reduce fluorescence quenching, which can then be quantified. Among other choices, it is often preferred that such assay is performed as an in vitro solid-phase based assay.

While such an assay is conceptually straightforward and can be used characterize BoNT/A, BoNT/C, or BoNT/E activity, such an assay cannot simply be modified to a cell-based assay for determination of BoNT/B activity by replacing the SNAP-25 motif with a SNARE domain, as the corresponding SNARE domain includes a membrane spanning sub-domain that would place an N-terminal fluorophore on the interior of a vesicle (thereby preventing energy transfer). In such case, only diffusion of the fluorescence signal would be observed (Dong et al. PNAS (2004), Vol. 101, No. 41, 14701-14706; United States Patent Publication No. 2006/0134722, to Chapman and Dong).

Other cell-based assays for botulinum neurotoxins are described in United States Patent Application Publication No. 2012/0322092 (to Tucker and Zeytin), and U.S. Pat. No. 9,274,121 (to Atapattu and Tucker). Cells utilized in such assays incorporate reporting constructs that include fluorescent peptide regions and botulinum neurotoxin (BoNT) substrate peptide regions, and are used to quantify BoNTs utilized as pharmaceutical compounds. In such cell-based assays reporting constructs expressed within the cells undergo measurable changes (for example, changes in the intensity or distribution of observed fluorescence) when exposed to an appropriate proteolytic activity. Such assays can utilize FRET to provide a fluorescence signal, or utilize detection of non-FRET mediated fluorescence (or the lack thereof) following degradation of the construct following cleavage by the botulinum neurotoxin. In such approaches, however, excessive persistence in the fluorescent emission of a fluorescent peptide following lysis of a reporting construct by a proteolytic enzyme can interfere with the results of the assays.

Approaches have been suggested to modulate the degree to which such reporting constructs are degraded within cells. Such approaches typically involve the insertion of degrons (i.e. short peptide sequences that increase the rate of degradation of a protein containing such sequences). For example, United States Patent Application Publication No. 2015/0010931 (to Oyler and Tsai) discusses application of the N-end rule to increase the rate of degradation of a product of proteolysis of a reporting construct. All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply. In such a construct the protease substrate peptide region is positioned near the N-terminus of the reporting construct and a fluorescent peptide region is positioned near the C-terminus. The protease substrate peptide sequence is selected so that proteolysis exposes an N-terminal amino acid associated with increased degradation rate, following the "N-end rule", leading to an increased rate of degradation for the fluorescent peptide. Oyler and Tsai teach the use of a substrate peptide region that is, essentially, a fragment of the substrate of the light chain of the BoNT expressed by serotype A *Clostridium botulinum*. United States Patent Application 2006/105953 (to LaCoste and Evans) teaches a similar reporting construct where the substrate peptide region is a caspase substrate. Such approaches, however, limit the selection of proteases and substrate peptide regions to sequences that provide the requisite N-terminal amino acid.

U.S. Pat. No. 9,249,449 (to Miyawaki and Hirano) discuss an alternative design for a reporting construct, in which an N-terminal fluorescent peptide is separate from a second fluorescent peptide by a proteolysis-terminating peptide, followed by a degradation-susceptible peptide positioned near the C-terminus. Degradation starting at the C-terminus, which can be mediated by the presence of a degron sequence, results in loss of the second fluorescent peptide and a measurable change in the observed fluorescence. Such an approach, however, limits reporting constructs to those that are degraded by specific intracellular mechanisms that respond to proteolysis-terminating peptide sequences.

Therefore, there is still a need for improved BoNT assays, and especially cell-based assays for BoNTs that cleave synaptobrevin.

SUMMARY OF THE INVENTION

The inventive subject matter provides compositions and methods for cell-based assays for specific protease activities, in particular botulinum neurotoxins. A pair of peptide constructs is provided where at least one of the pair incorporates a cleavage site for the protease activity. The pair of peptide constructs include sequences that provide co-localization of the members of the pair and detectable labels (e.g. peptides derived from GFP or GFP mutants). Cleavage results in release of detectable label, followed by degradation of the released label. Peptide constructs can include sequences that enhance or increase the rate of this degradation, for example degron sequences. In some embodiments one member of the pair of peptide constructs includes mutations that prevent or reduce the rate of cleavage by the specific protease activity, leading to retention of an associated label. Such a retained or otherwise non-labile label can be used for data normalization.

One embodiment of the inventive concept is a reporting construct for characterizing botulinum serotype neurotoxin that includes a first reporter peptide having a first membrane binding peptide configured to localize to a vesicle membrane, a first fluorescent peptide, and a first linking peptide derived from synaptobrevin positioned between the first membrane binding peptide and the first fluorescent peptide, and also a second reporter peptide having a second membrane binding peptide configured to localize to a vesicle membrane, a second fluorescent peptide, and a second linking peptide derived from synaptobrevin positioned between the second membrane binding peptide and the second fluorescent peptide. In such a construct the first fluorescent peptide and the second fluorescent peptide (which can be derived from GFP or a GFP mutation) are positioned such that no useful (e.g. less than about 5%) Forster resonance energy transfer (FRET) occurs between them. Such peptides can be encoded on a single plasmid, or can be encoded on separate and distinct plasmids. In some embodiments the first linking region incorporates one or more mutations that decrease susceptibility to proteolysis by botulinum B neurotoxin, for example a point mutation of an amino acid that forms part of a botulinum serotype B neurotoxin cleavage site and/or an exosite of synaptobrevin (e.g. D64N, D65N, D68N, and Q76V mutations of synaptobrevin). In some embodiments the first fluorescent peptide and the second fluorescent peptide have distinguishably different emission frequencies. In such embodiments the reporting constructs the first fluorescent peptide and/or the second fluorescent peptide can include one or more mutations that increase the rate of intracellular proteolysis relative to an analogous peptide that does not incorporate the one or more mutations. Examples of suitable mutations include a point mutation that replaces a native amino acid with a basic amino acid and inclusion of a degron sequence. Such reporting constructs can be expressed in a cell, such as a Neuro2A cell, M17 cell, PC12 cell, SK-N-SH cell, LNCaP cell, an immortalized murine astrocyte, a human and/or murine hTERT immortalized cell, an iPSC neuron, a stem cell derived neuron, and/or a primary neuron.

Another embodiment of the inventive concept is a method for characterizing an analyte (such as a botulinum neurotoxin) by (1) providing a field comprising a plurality of spatially distinct testing regions (for example, a population of cells), (2) obtaining a first image of the field prior to exposure to the analyte, where the first image provides a measure of intensity of a first signal, (3) identifying (within the first image) one or more of the spatially distinct testing regions wherein the intensity of the first signal lies within a range delimited by a designated minimum value and a designated maximum value, (4) generating a quantitation mask representing one or more areas within the image delimited by the minimum value and the maximum value, (5) recording a first intensity value within an area of the first image defined by the quantitation mask, (6) contacting the field with a sample containing the analyte, (7) obtaining a second image of the field, (8) recording a second intensity value within an area of the second image defined by the quantitation mask, (9) generating a first result by combining the first intensity value with total area represented by the quantitation mask, (10) generating a second result by combining the second intensity value with total area represented by the quantitation mask, and (11) comparing the second result with the first result. In such a method the first result can be obtained by multiplying the first intensity value by total area represented by the quantitation mask and the second result can be obtained by multiplying the second intensity value by total area represented by the quantitation mask. Examples of cells suitable for this purpose include Neuro2A cells, M17 cells, PC12 cells, SK-N-SH cells, LNCaP cells, immortalized murine astrocytes (for example, SV40T cells), human and/or murine hTERT immortalized cells, iPSC neurons, stem cell derived neurons, and/or primary neurons. In some embodiments the minimum value represents a minimum fluorescence intensity that is distinguishable from background fluorescence. Similarly, the maximum value can represents a value characteristic of saturation of a detection device utilized to acquire the first image, or can represent a value beyond which a detection device utilized to acquire the first image departs from linearity between detection device response and light intensity.

Another embodiment of the inventive concept is a reporting peptide construct that has an N-terminus and a C-terminus, a degron positioned at or near the N-terminus, a localization sequence positioned at or near the C-terminus of the reporting peptide, a signaling sequence positioned proximal to the degron, and a protease substrate sequence positioned between the signaling sequence and the localization sequence. In such a reporting construct the localization sequence is selected to localize the reporting peptide in a protected region of a cell. Suitable degron sequences include an amino acid selected according to the N-end rule and degrons associated with peptides such as Bonger (SEQ ID NO. 11), TAZ (SEQ ID NO. 12), HIF-α (SEQ ID NO. 13), iNOS (SEQ ID NO. 14), SRC3 (SEQ ID NO. 15), Cyclin D1 (SEQ ID NO. 16), IFNAR1 (SEQ ID NO. 17), p53 (SEQ ID NO. 18), β-catenin (SEQ ID NO. 19), and SNAP-25 (SEQ ID NO. 10). In such embodiments the localization sequence can be selected to localize the reporting peptide at a membrane (e.g. a plasma membrane, a rough ER membrane, a smooth ER membrane, a vesicle membrane, and/or a nuclear membrane) and can be a part of or include a protease substrate sequence (and/or cleavage site), for example a BoNT substrate protein. In some embodiments the signaling sequence includes a fluorescent peptide sequence, for example a peptide sequence that has at least 80% sequence identity to green fluorescent protein (GFP). In some embodiments the protease substrate sequence comprises all or a portion of a BoNT substrate sequence, for example a BoNT/A substrate sequence, a BoNT/B substrate sequence, a BoNT/C substrate sequence, a BoNT/D substrate sequence, a BoNT/E substrate sequence, a BoNT/F substrate sequence, and a BoNT/G substrate sequence.

Another embodiment of the inventive concept is a cell (such as a neuron or neuronally-derived cell) that incorporates a reporting peptide construct that has an N-terminus and a C-terminus, a degron positioned at or near the N-terminus, a localization sequence positioned at or near the C-terminus of the reporting peptide and is selected to localize the reporting peptide in a protected region of the cell, a signaling sequence positioned proximal to the degron, and a protease substrate sequence positioned between the signaling sequence and the localization sequence. In such a reporting construct the localization sequence is selected to localize the reporting peptide in a protected region of a cell. Suitable degron sequences include an amino acid selected according to the N-end rule and degrons associated with peptides such as Bonger (SEQ ID NO. 11), TAZ (SEQ ID NO. 12), HIF-α (SEQ ID NO. 13), iNOS (SEQ ID NO. 14), SRC3 (SEQ ID NO. 15), Cyclin D1 (SEQ ID NO. 16), IFNAR1 (SEQ ID NO. 17), p53 (SEQ ID NO. 18), β-catenin (SEQ ID NO. 19), and SNAP-25 (SEQ ID NO. 10). In such embodiments the localization sequence can be selected to localize the reporting peptide at a membrane (e.g. a plasma membrane, a rough ER membrane, a smooth ER membrane, a vesicle membrane, and/or a nuclear membrane) and can be a part of or include a protease substrate sequence (and/or cleavage site), for example a BoNT substrate protein. In some embodiments the signaling sequence includes a fluorescent peptide sequence, for example a peptide sequence that has at least 80% sequence identity to green fluorescent protein (GFP). In some embodiments the protease substrate sequence comprises all or a portion of a BoNT substrate sequence, for example a BoNT/A substrate sequence, a BoNT/B substrate sequence, a BoNT/C substrate sequence, a BoNT/D substrate sequence, a BoNT/E substrate sequence, a BoNT/F substrate sequence, and a BoNT/G substrate sequence.

Another embodiment of the inventive concept is a method of characterizing an analyte (for example, a botulinum neurotoxin or BoNT) by (1) obtaining a cell comprising a reporting construct having an N-terminus and a C-terminus, a degron positioned at or near the N-terminus of the reporting peptide, a localization sequence positioned at or near the C-terminus of the reporting peptide, a signaling sequence positioned proximal to the degron, and a protease substrate sequence positioned between the signaling sequence and the localization sequence, where the localization sequence is selected to localize the reporting peptide in a protected region of the cell, (2) contacting the cell with the analyte, wherein presence of the analyte results in an intracellular proteolytic activity within the cell that is directed towards the protease substrate sequence, and (3) obtaining a signal from the signaling sequence. In such an embodiment the degron can include an amino acid selected according to the N-end rule and/or a degron sequence derived from Bonger (SEQ ID NO. 11), TAZ (SEQ ID NO. 12), HIF-α (SEQ ID NO. 13), iNOS (SEQ ID NO. 14), SRC3 (SEQ ID NO. 15), Cyclin D1 (SEQ ID NO. 16), IFNAR1 (SEQ ID NO. 17), p53 (SEQ ID NO. 18), β-catenin (SEQ ID NO. 19), and SNAP-25 (SEQ ID NO. 10). In such a method the localization sequence can be selected to localize the reporting peptide at a membrane, such as a plasma membrane, a rough ER membrane, a smooth ER membrane, a vesicle membrane, and/or a nuclear membrane, and can be part of or include the protease substrate sequence (for example, a BoNT substrate protein). Suitable protease substrate sequences include a BoNT/A substrate sequence, a BoNT/B substrate sequence, a BoNT/C substrate sequence, a BoNT/D substrate sequence, a BoNT/E substrate sequence, a BoNT/F substrate sequence, and a BoNT/G substrate sequence. In such embodiments the signaling sequence can be a fluorescent peptide sequence, for example a peptide having at least 80% sequence identity to green fluorescent protein.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIGS. 6A and 6B show a pMD0032 ORF encoding a YFP-synaptobrevin (VAMP2) peptide (SEQ ID NO. 1). The sequence shown in FIG. 6B continues from the sequence shown in FIG. 6A.

FIGS. 7A and 7B show a pMD0034 ORF encoding another YFP-synaptobrevin (VAMP2) peptide (SEQ ID NO. 3). The sequence shown in FIG. 7B continues from the sequence shown in FIG. 7A.

FIGS. 8A and 8B. show a different pMD0034 ORF, encoding a CFP-VAMP2 peptide (SEQ ID NO. 2). The sequence shown in FIG. 8B continues from the sequence shown in FIG. 8A.

FIGS. 9A and 9B show a pMD0071 ORF encoding for another YFP-VAMP2 peptide (SEQ ID NO. 5). The sequence shown in FIG. 9B continues from the sequence shown in FIG. 9A.

FIGS. 10A and 10B show a different pMD0071 ORF, encoding for an ECFP-synaptobrevin (VAMP2) (Q76V) peptide (SEQ ID NO. 4). The sequence shown in FIG. 10B continues from the sequence shown in FIG. 10A.

FIGS. 11A, 11B, 11C and 11D show a pMD0183 ORF encoding for a YFP-YFP-synaptobrevin (VAMP2) peptide (SEQ ID NO. 8), which incorporates two YFP peptides arranged sequentially. The sequence shown in FIG. 11B continues from the sequence shown in FIG. 11A. The sequence shown in FIG. 11C continues from the sequence shown in FIG. 11B and is continued in FIG. 11D.

FIGS. 12A and 12B show a pMD0185 ORF encoding for another YFP-synaptobrevin (VAMP2) peptide (SEQ ID NO. 7). The sequence shown in FIG. 12B continues from the sequence shown in FIG. 12A.

FIGS. 13A and 13B show a different pMD0185 ORF, encoding for a CFP-synaptobrevin (VAMP2) (D64N, D68N, Q76V) peptide (SEQ ID NO. 6). The sequence shown in FIG. 13B continues from the sequence shown in FIG. 13A.

FIG. 15A shows a reporting construct pair that does not include a degron sequence position towards the N-terminus relative to a reporting fluorophore (e.g. YFP). FIG. 15B shows a reporting construct pair that includes a degron sequence position towards the N-terminus relative to a reporting fluorophore (e.g. YFP).

FIG. 16A provides a photomicrograph of cells expressing a control (i.e. no degron sequence) reporting construct pair in the presence and absence of BoNT/B. FIG. 16B shows the overall fluorescence emission from cells such as those shown in FIG. 16A as characterized using a fluorescence plate reader.

FIG. 17A shows measurements of YFP emission in the presence and absence of BoNT/B. FIG. 17B shows measurements of CFP emission in the presence and absence of BoNT/B. FIG. 17C shows results of measurements of YFP fluorescence:CFP fluorescence ratio in the presence and absence of BoNT/B.

FIG. 18A shows measurements of YFP emission in the presence and absence of BoNT/B. FIG. 18B shows measurements of CFP emission in the presence and absence of BoNT/B. FIG. 18C shows results of measurements of YFP fluorescence:CFP fluorescence ratio in the presence and absence of BoNT/B.

FIG. 19A shows brightfield, YFP emission, and CFP emission photomicrographs of transformed cells expressing a control reporting construct pair (containing no degron sequence) and transformed cells expressing reporting construct pairs that include degron sequences (specifically, Bonger or iNOS degron sequences) positioned N-terminally to the YFP peptide of the YFP-bearing member of the reporting construct pair. FIG. 19B shows the results of studies similar to those shown in FIG. 12A, but performed using cells carrying either the pMD0191 or pMD0192 reporting construct pairs, both of which show improved dynamic range on exposure to BoNT/B relative to control cell.

FIG. 20 shows results of application of BoNT/B at different concentrations to cells expressing a control BoNT/B-reactive construct pair lacking a degron sequence and cells expressing analogous BoNT/B-reactive construct pair where the YFP-bearing peptide includes a degron sequence.

DETAILED DESCRIPTION

Figure 1:
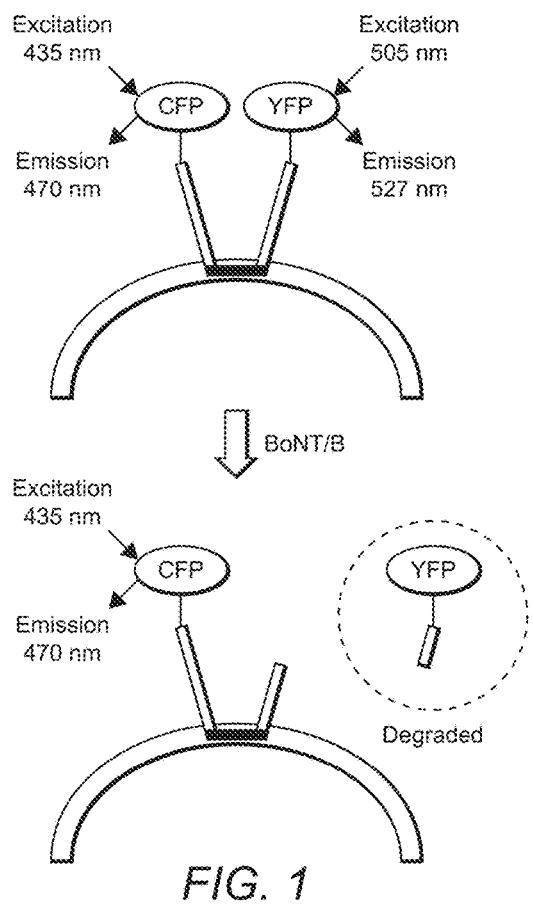
FIG. 1 shows an exemplary arrangement of the components of a reporting construct of the inventive concept.

The inventive subject matter provides compositions and methods in which reporting constructs and quantitation methods are described that are useful in characterizing botulinum B neurotoxin (BoNT/B) using cell based assays. Cells are transformed, either transiently or permanently to express a reporting construct that includes one or more fluorescing peptide domains. In instances where two or more fluorescing peptide domains are provided, they are arranged so that no useful Forster resonance energy transfer (FRET) occurs between fluorescing peptides (i.e. less than 25%, 20%, 15%, 10%, 5%, 2.5%, or 1% energy transfer). Such reporting constructs include a membrane targeting region derived from synaptobrevin, which is selective for vesicle membranes, thereby anchoring the reporting construct to a vesicle. A cleavage and recognition site that serves as a BoNT/B substrate is positioned such that BoNT/B light chain activity releases one or more fluorescent peptide portions of the reporting construct into the cytosol. Such reporting constructs are expressed in cells that include cell surface receptors that facilitate uptake of BoNT/B, and the resulting changes in fluorescence observed in such cells on exposure to BoNT/B can be utilized in characterization of the neurotoxin.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

A reporting construct of the inventive construct can incorporate one or more amino acids or amino acid sequences (e.g. degron sequences) that enhance degradation of at least a portion of the reporting construct. For example, a reporting construct can include one or more degron sequence(s) positioned at or near the N-terminus of the reporting construct. A reporting peptide construct can, for example, produce a detectable signal (for example, a fluorescent peptide) from a region that is positioned adjacent to a degron sequence and is interposed between the degron sequence and a protease substrate sequence (which can be positioned at or near the C-terminus of the reporting construct). Such a protease substrate sequence can include one or more protease recognition sequences, one or more protease cleavage sites (which can be distinct from or essentially to the protease recognition sequences), and/or a localization sequence.

Alternatively, a localization sequence can be provided that is distinct from the protease substrate sequence and positioned between the protease substrate sequence and the C terminus of the reporting construct. Such a localization sequence serves to localize the intact reporting construct in a protected site, within which a reporting construct is protected or at least partially protected from an intracellular protein degradation system that interacts with a degron sequence of the reporting construct. On exposure to the protease activity being characterized a cleavage event occurs within the protease substrate sequence, release a fragment of the reporting construct that includes the degron sequence and the reporting peptide sequence from the protected site. Release from the protected site results in rapid degradation of the reporting peptide sequence (i.e. occurring at an elevated rate relative to the reporting sequence alone within the same intracellular environment), resulting in a rapid change in the observed detectable signal.

One should appreciate that the disclosed techniques provide many advantageous technical effects including providing highly sensitive testing for characterization of BoNT/B neurotoxin that provides a high degree of correlation to animal-based testing while relying on cultured cells. In addition, the disclosed methods and compositions provide reduced interference in such cell-based assay results from released, but undegraded, fragments of the reporting construct. This reduced interference can improve sensitivity and/or reduce time to first result in a cell-based assay.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

One embodiment of the inventive concept is a reporting construct arranged as a single peptide that includes a first fluorescent peptide region, a synaptobrevin derived membrane binding region, a BoNT/B recognition and cleavage site, and a second fluorescent peptide. The first and second fluorescent peptide can have distinct excitation and emission spectra, and are arranged so that no significant FRET occurs between them. In a preferred embodiment the BoNT/B recognition and cleavage site is derived from synaptobrevin. Cleavage of the recognition and cleavage site results in release of one of the fluorescent peptides into the cytosol, where it can be subsequently degraded. In some embodiments one or both of the fluorescent peptides can include amino acid sequence modifications (such as incorporation of basic amino acids and/or degron sequences) that enhance degradation of the released peptide fragment on release into the cytosol. FIG. 1 shows an exemplary arrangement of the components of such a reporting construct.

In a preferred embodiment of the inventive concept a fluorescent peptide utilized in the construct is derived from green fluorescent protein (GFP) or a GFP mutation. Suitable GFP mutations include EGFP, EBFP, EBFP2, Azurite, mKalama1, CFP, ECFP, Cerulean, CyPet, mTurqoise, YFP, Citrine, Venus, and/or YPet. It should be appreciated that in some embodiments one member of the fluorescent peptide pair can be retained on the vesicle membrane on exposure of a cell expressing the construct to BoNT/B. In embodiments where one of the fluorescent peptides is retained on the vesicle membrane following proteolysis by BoNT/B light chain (or otherwise not degraded following exposure of the cell to a BoNT), emission measurement from the retained fluorescent peptide can be used to normalize emission measurements made from the release fluorescent peptide. For example, fluorescence emission from such a retained fluorescent peptide can be used to normalize results for differences in gene expression, cell number, and/or cell distribution within different test sites or test wells of an assay test fixture (such as a multiwell test plate). Alternatively, fluorescence emission from such a retained fluorescent peptide can be utilized as an identifying feature in an artificial vision system, for example an artificial vision system utilizing an algorithm that identifies specific features of interest (e.g. labeled cell and/or intracellular components) within an image obtained from a test area. In embodiments where both fluorescent peptides are released from the vesicle membrane by the action of BoNT/B light chain proteolytic activity data, similar normalization can be provided by the application of a reference dye (for example, a fluorescent cell membrane-binding dye with a distinguishable excitation and emission spectra).

Figure 2:
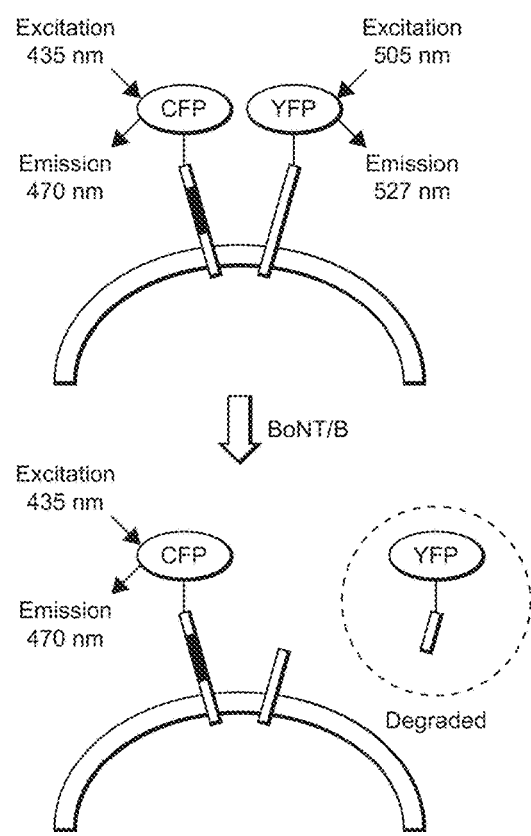
FIG. 2 shows an example of a reporting construct pair of the inventive concept.

In another embodiment of the inventive concept a pair of reporting constructs are utilized. In such an embodiment each member of the pair includes a synaptobrevin-derived membrane binding portion and a fluorescent peptide, with each member of the pair carrying a distinct fluorescent peptide. One member of the peptide pair includes a BoNT/B cleavage and recognition site (such as synaptobrevin or a synaptobrevin-derived peptide) interposed between the membrane binding portion and the fluorescent peptide. The remaining member of the peptide pair includes a peptide that is interposed between the membrane binding portion and the fluorescent peptide, but that does not act as a BoNT/B recognition and cleavage site. Such a peptide can be, for example, synaptobrevin or a synaptobrevin-derived peptide which includes amino acid substitutions at the BoNT/B proteolytic cleavage site and/or outlying BoNT/B recognition sites (e.g. exosites). As a result such a member of the peptide pair can retain localization, complex formation, and other characteristics of synaptobrevin, but is not cleaved by BoNT/B activity. As a result the associated fluorophore is retained on the vesicle membrane. It should be appreciated that, unlike BoNT peptides such as those reported in U.S. Pat. No. 9,624,529 (to Oyler and Tsai), use of such peptide pairs incorporating a non-cleavable member provides for an internal control useful in data normalization. In some embodiments significant (i.e. greater than 5% energy transfer) can occur between the fluorophores of a reporting construct pair. In other embodiments, while the different fluorescent peptides of the reporting construct can have distinct excitation and emission spectra the pair of fluorescent peptides is arranged such that no significant FRET occurs between them. It should be appreciated that such a lack of significant (i.e. greater than 5%) energy transfer between the fluorescent peptide can reduce or eliminate quenching effects associated with FRET, which in turn can improve the utility of a signal obtained from a retained (or otherwise non-labile) fluorescent peptide for data normalization. Cleavage of the BoNT/B recognition and cleavage site results in the release of one of the fluorescent peptides into the cytosol, where it is subsequently degraded. As noted above, such a released fluorescent peptide can be associated with amino acids and or amino acid sequences that enhance the rate of degradation on release into the cytosol (relative to a corresponding peptide that lacks a degradation-enhancing amino acid or amino acid sequence). FIG. 2 shows an example of such a reporting construct pair.

Figure 3:
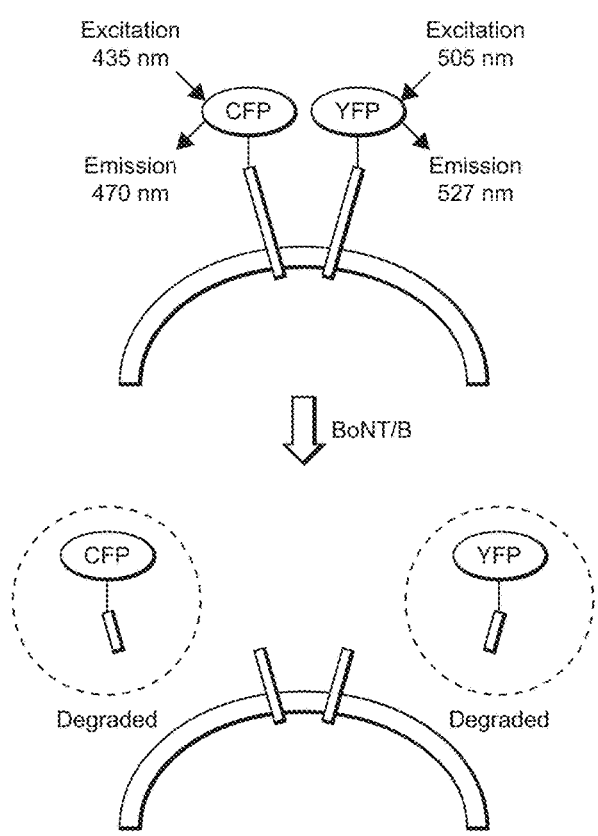
FIG. 3 shows another example of a reporting construct pair of the inventive concept.

In another embodiment of the inventive concept a pair of reporting constructs are utilized. In such an embodiment each member of the pair includes a synaptobrevin-derived (i.e. corresponding to a portion of the synaptobrevin amino acid sequence and/or having greater than about 80% sequence identity with synaptobrevin) membrane binding portion, a BoNT/B recognition and cleavage site (for example, synaptobrevin or a synaptobrevin-derived peptide) and a fluorescent peptide, with each member of the pair carrying a distinct fluorescent peptide. One member of the peptide pair includes a BoNT/B cleavage and recognition site (such as synaptobrevin or a synaptobrevin-derived peptide) interposed between the membrane binding portion and the fluorescent peptide. While the distinct fluorescent peptides can have distinct excitation and emission spectra, the construct pair is arranged such that no significant FRET occurs between them, as noted above. Cleavage of the BoNT/B recognition and cleavage site results in the release of one or both of the fluorescent peptides into the cytosol, followed by degradation of the released peptide(s). As noted above, such released fluorescent peptides can include an amino acid or an amino acid sequence (e.g. a degron sequence) that enhances the rate of degradation following release into the cytosol relative to a corresponding peptide lacking such an amino acid or amino acid sequence. FIG. 3 shows an example of such a reporting construct pair.

In a preferred embodiment of the inventive concept a fluorescent peptide utilized in the construct is derived from green fluorescent protein (GFP) or a GFP mutation. It should be appreciated that in some embodiments one member of the fluorescent peptide pair can be retained on the vesicle membrane on exposure of a cell expressing the construct to BoNT/B. In embodiments where one of the fluorescent peptides is retained on the vesicle membrane following proteolysis by BoNT/B light chain, emission measurement from the retained fluorescent peptide can be used to normalize emission measurements made from the release fluorescent peptide. In embodiments where both fluorescent peptides are released from the vesicle membrane by the action of BoNT/B light chain proteolytic activity data normalization can be provided by the application of a reference dye (for example, a fluorescent cell membrane-binding dye with a distinguishable excitation and emission spectra).

Figure 4:
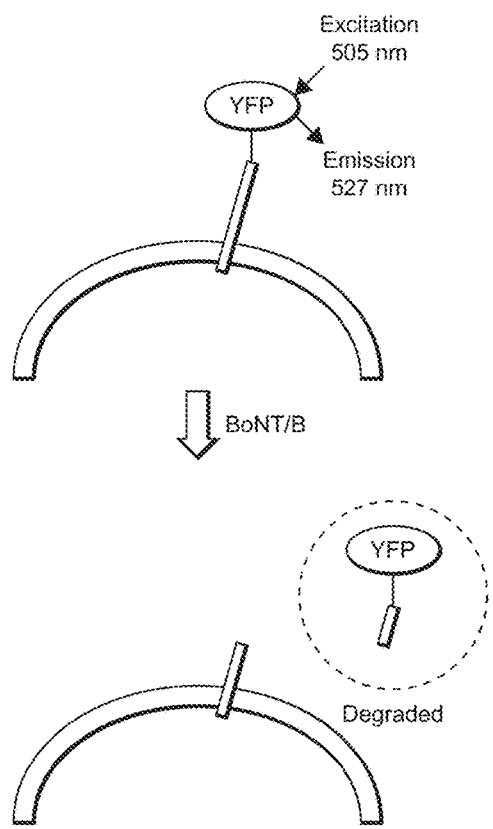
FIG. 4 shows an exemplary arrangement of the components of a reporting construct of the inventive concept.

In another embodiment of the inventive concept the reporting construct arranged as a single peptide that includes a synaptobrevin derived membrane binding region, a BoNT/B recognition and cleavage site, and a fluorescent peptide region. In a preferred embodiment the BoNT/B recognition and cleavage site is derived from synaptobrevin. Cleavage of the recognition and cleavage site results in release of the fluorescent peptide into the cytosol, where it can be subsequently degraded. In some embodiments the fluorescent peptide can include amino acid sequence modifications (such as incorporation of basic amino acids and/or a degron sequence) that enhance degradation on release into the cytosol relative to a corresponding peptide lacking such an amino acid or degron sequence. FIG. 4 shows an exemplary arrangement of the components of such a reporting construct.

In a preferred embodiment of the inventive concept a fluorescent peptide utilized in the construct is derived from green fluorescent protein (GFP) or a GFP mutation. In some embodiments data normalization can be provided by the application of a reference dye (for example, a fluorescent cell membrane-binding dye with a distinguishable excitation and emission spectra).

Figure 5:
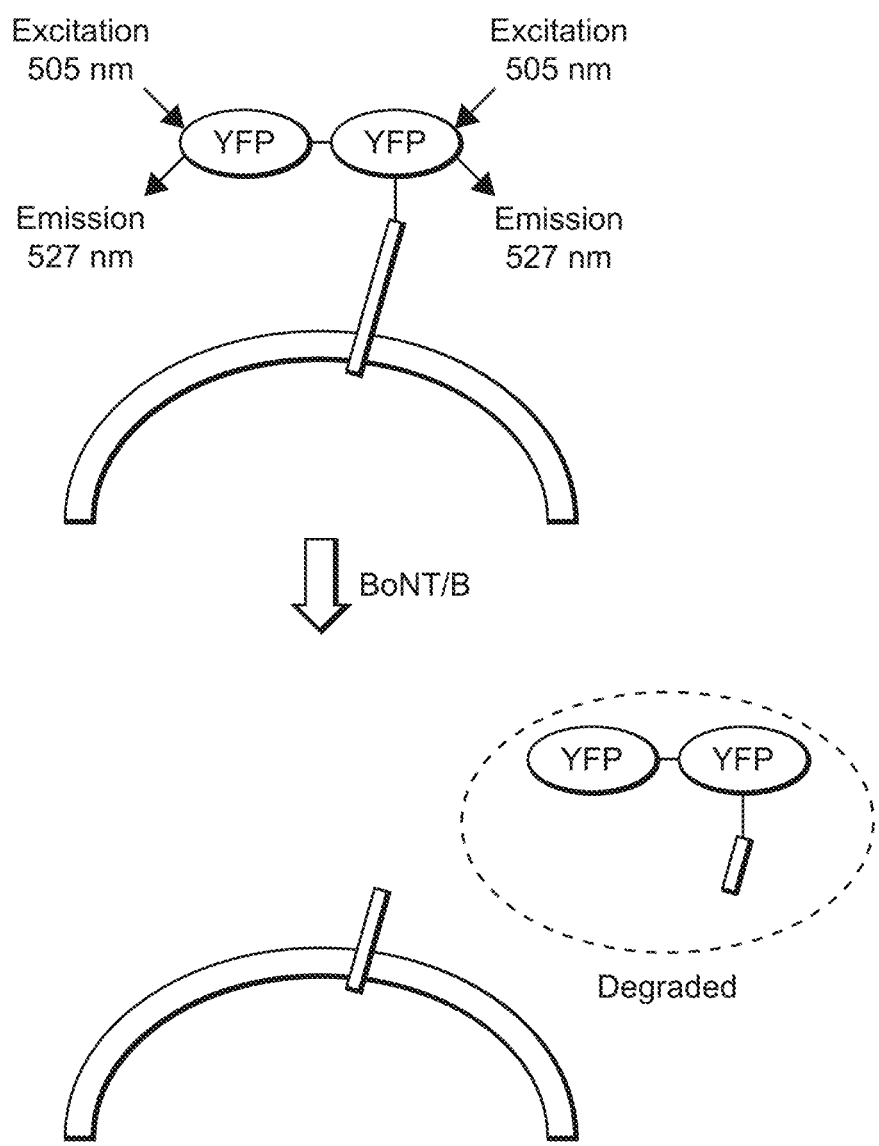
FIG. 5 shows another exemplary arrangement of the components of a reporting construct of the inventive concept.

In another embodiment of the inventive concept the reporting construct arranged as a single peptide that includes a synaptobrevin derived membrane binding region, a BoNT/B recognition and cleavage site, and a fluorescent peptide region that includes at least two identical fluorescing peptides linked to one another by a spacer peptide. Such a spacer peptide is purely structural and does not fluoresce, does not act as a BoNT/B substrate, and does not have a membrane binding function. In a preferred embodiment the BoNT/B recognition and cleavage site is derived from synaptobrevin. Cleavage of the recognition and cleavage site results in release of the fluorescent peptide region into the cytosol, where it can be subsequently degraded. As noted above, such a released fluorescent peptide can include an amino acid or amino acid sequence (e.g. a degron sequence) that enhances the rate of degradation relative to a corresponding peptide lacking such an amino acid or amino acid sequence. In some embodiments one or more of the fluorescent peptides can include amino acid sequence modifications (such as incorporation of basic amino acids) that enhance degradation on release into the cytosol. FIG. 5 shows an exemplary arrangement of the components of such a reporting construct.

Reporting constructs as described above can be expressed in cells that have been transformed and/or transduced (e.g. utilizing a virus), either transiently or permanently. As such, they can be encoded on one or more plasmids. In some embodiments such plasmids can be incorporated and/or integrated into the genome of a bacterial, fungal, or eukaryotic cell. In embodiments of the inventive concept that utilize two different peptides, both peptides can be encoded on a single plasmid. In other embodiments that utilize two different peptides, each peptide can be encoded on different plasmids. In such an embodiment the plasmids can include identical regulatory elements, or can include different regulatory elements that permit differential expression of the peptides.

Cells suitable for use in methods of the inventive concept include cells that are susceptible to BoNT/B intoxication. Such cells can include cell surface receptors for BoNT/B. Suitable cells can be presented as cells in cell culture (either primary or as cultured cell lines), and can be neuronal cells or derived from neuronal cells (for example, from tumors derived from neuronal cells). Alternatively suitable cells can include non-neuronally derived cells that have been modified, permanently or transiently, to express or otherwise possess suitable cell surface receptors. Suitable cells can be of human or animal (e.g. murine or rat) origin, and can include retinoblastoma cells, Neuro2A cells, M17 cells, PC12 cells, SK-N-SH cells, LNCaP cells, immortalized murine astrocytes (for example, SV40T cells), human and/or murine hTERT immortalized cells, iPSC neurons, stem cell derived neurons, and/or primary neurons.

As noted above, constructs of the inventive concept can be encoded on plasmids, which can in turn be used in the temporary and/or permanent transformation of cells. In instances where the reporting construct system includes a pair of reporter peptides, both can be encoded on a single plasmid. Alternatively, in some embodiments of the inventive concept the peptides of a reporting construct system that utilizes a pair of reporter peptides can be encoded on different plasmids. Examples of suitable peptides are shown in FIGS. 6 to 13. A plasmid pMD0032 ORF (SEQ ID NO. 1) encodes for a YFP-synaptobrevin (VAMP2) peptide (FIGS. 6A and 6B). A plasmid pMD0034 ORF encodes for another YFP-synaptobrevin (VAMP2) peptide (SEQ ID NO. 3; FIGS. 7A and 7B) and another pMD0034 ORF encodes for a CFP-synaptobrevin (VAMP2) peptide (SEQ ID NO. 2; FIGS. 8A and 8B). A plasmid pMD0071 ORF encodes for another YFP-synaptobrevin (VAMP2) peptide (SEQ ID NO. 5; FIGS. 9A and 9B) and pMD0071 ORF encodes for an ECFP-synaptobrevin (VAMP2) (Q76V) peptide (SEQ ID NO. 4; FIGS. 10A and 10B, which is not cleaved by BoNT/B). A plasmid pMD0183 ORF encodes for a YFP-YFP-synaptobrevin (VAMP2) peptide (SEQ ID NO. 8; FIGS. 11A and 11B), which includes two YFP peptide sequences arranged in series. A plasmid pMD0185 ORF encodes for another YFP-synaptobrevin (VAMP2) peptide (SEQ ID NO. 7; FIGS. 12A and 12B) and another pMD0185 ORF encodes for a CFP-synaptobrevin (VAMP2) (D64N, D68N, Q76V) peptide (SEQ ID NO. 6; FIGS. 13A and 13B, which is not cleaved by BoNT/B).

Figure 14:
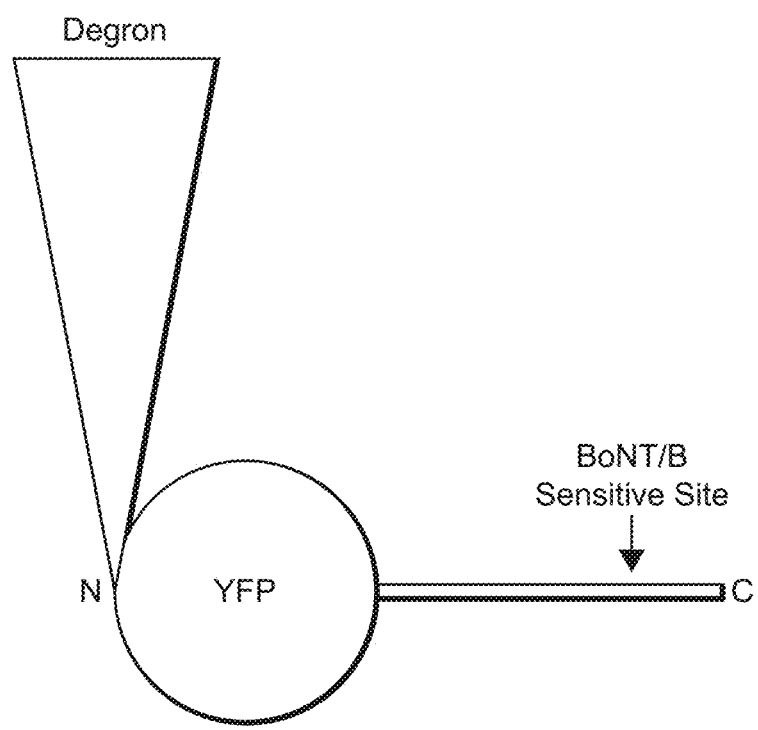
FIG. 14 depicts a typical reporting construct utilized in the characterization of a BoNT from a serotype B *Clostridium botulinum* (BoNT/B).
Figure 15A:
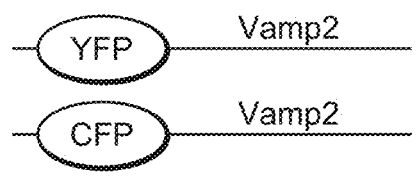
FIGS. 15A and 15B schematically depict reporting construct pairs of the inventive concept.
Figure 15B:
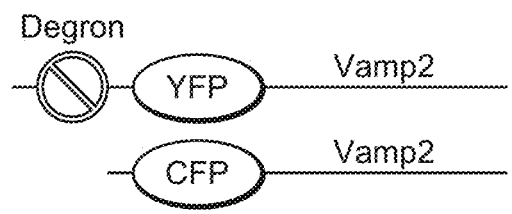
Figure 16A:
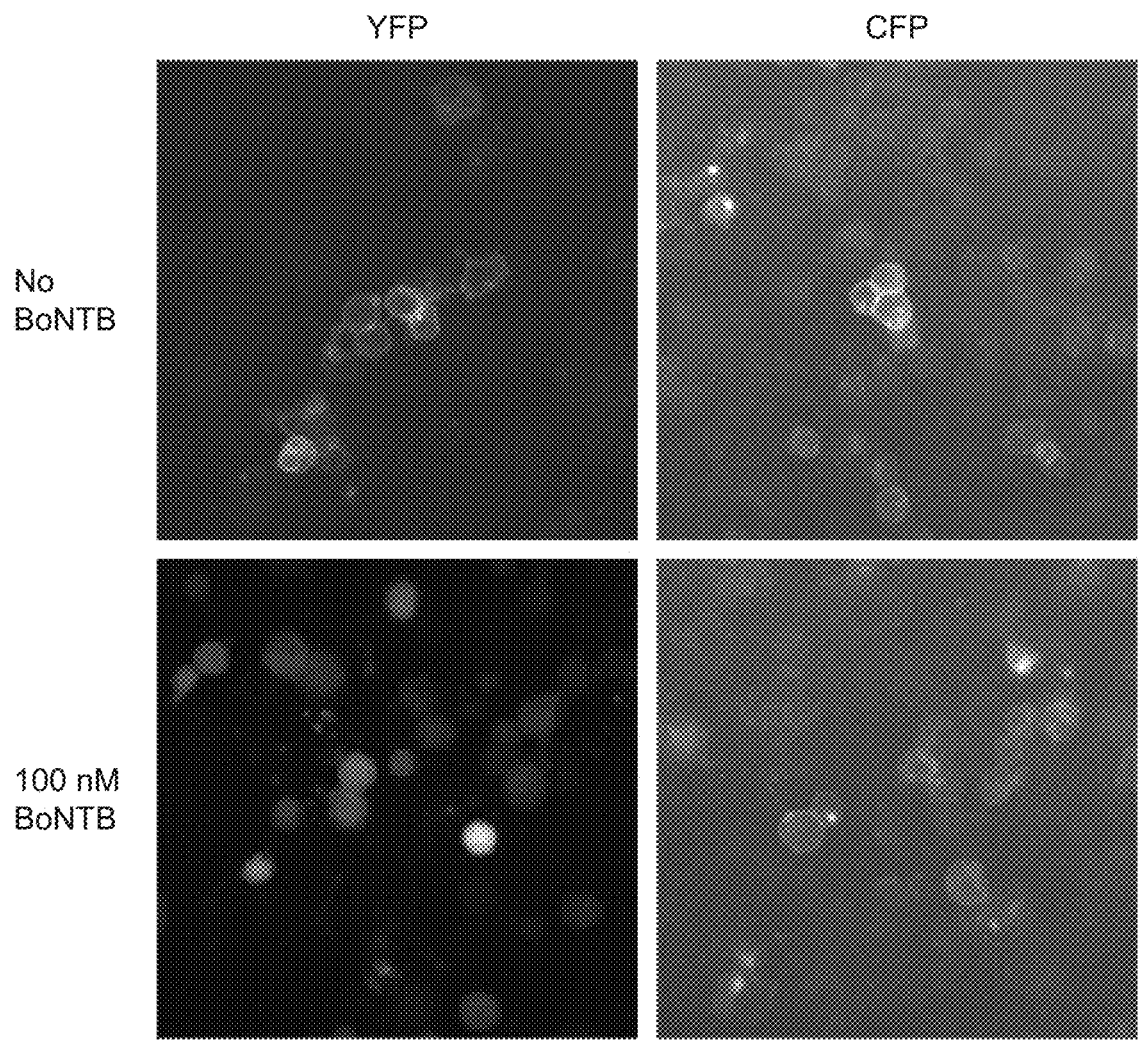
FIGS. 16A and 16B show the results of exposure of transformed cells carrying reporting construct pairs of the inventive concept to BoNT/B.
Figure 16B:
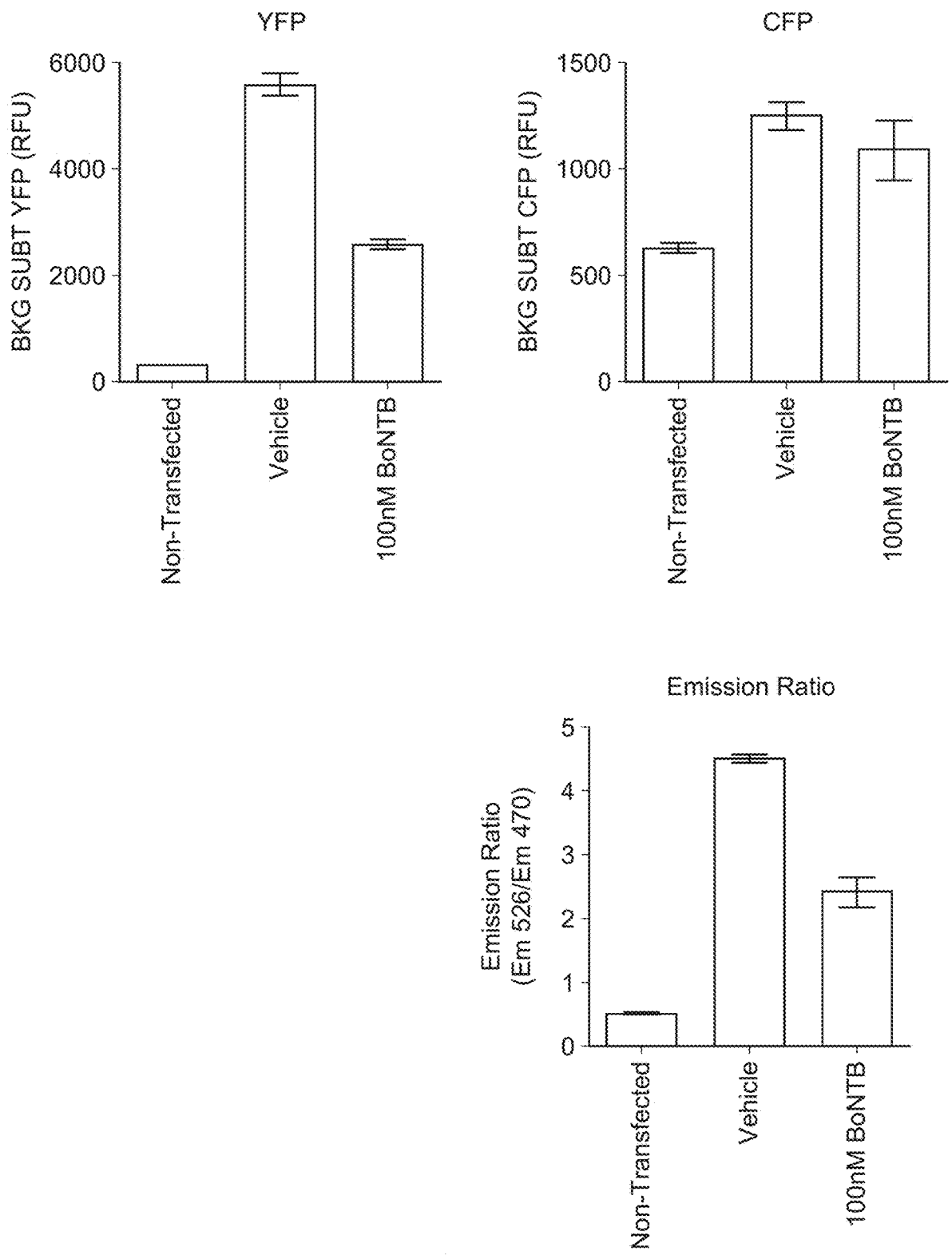
Figure 17A:
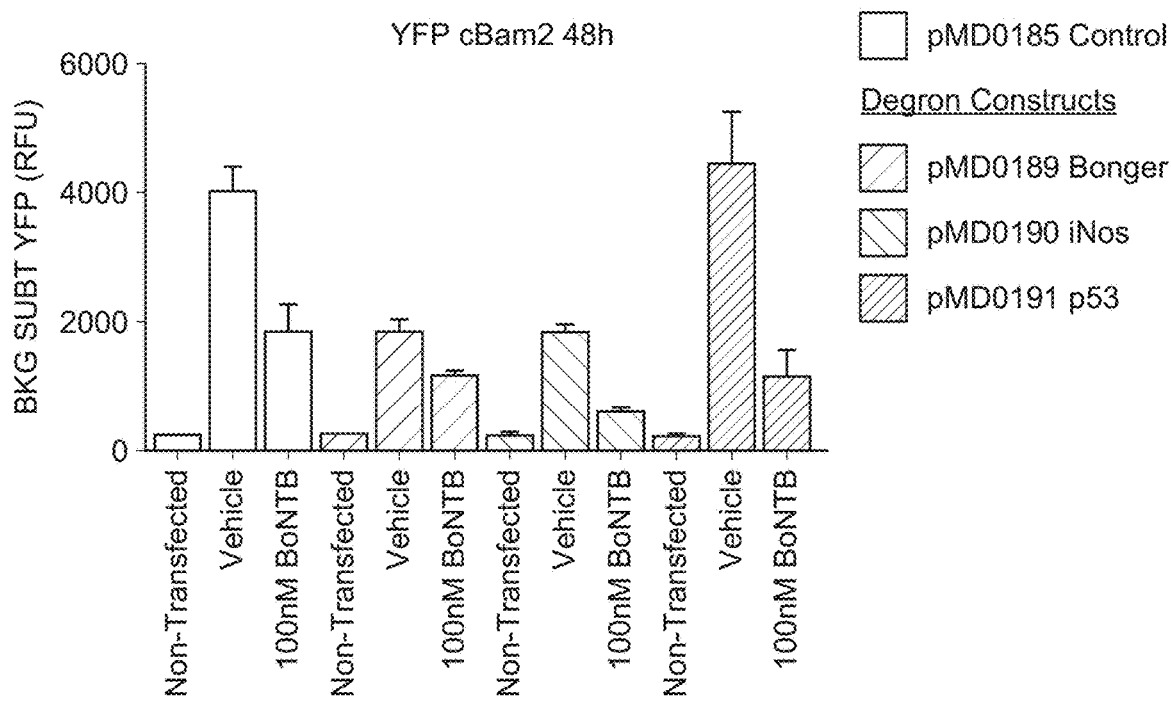
FIGS. 17A to 17C show the results of fluorescence measurements made from non-transformed cells, cells transformed to express a control (i.e. not containing degron) reporting construct pair, and cells transformed to express reporting construct pairs in which the YFP-bearing construct included a degron sequence positioned towards the N-terminus relative to the YFP peptide.
Figure 17B:
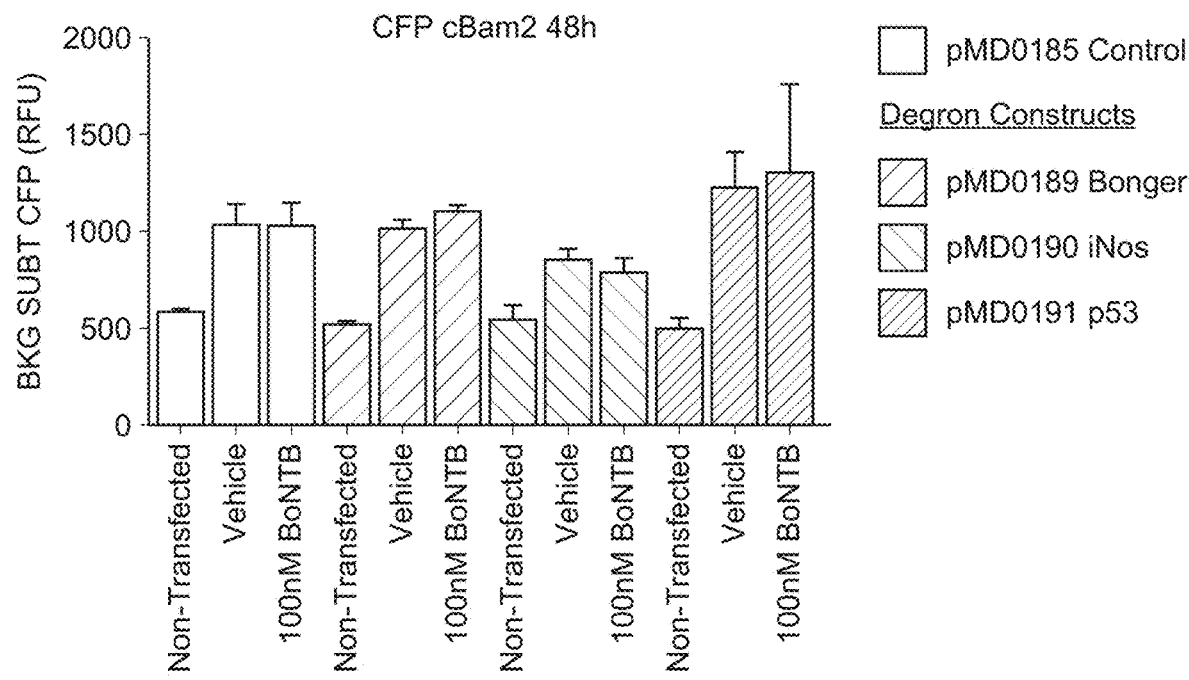
Figure 17C:
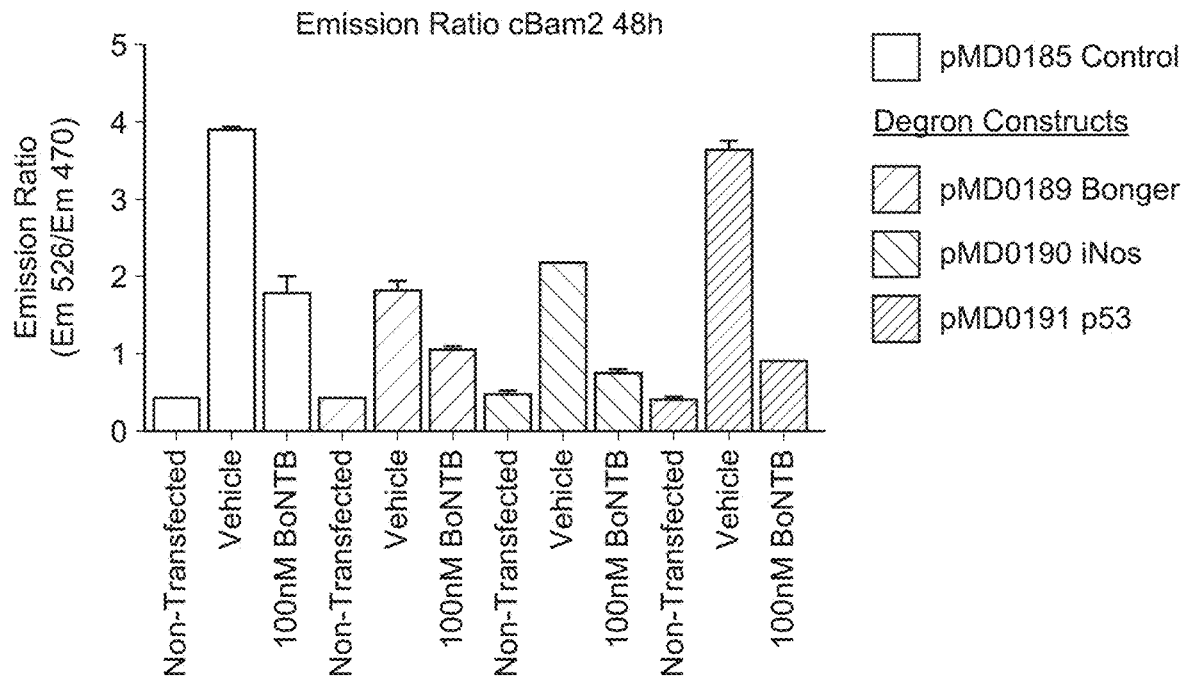

In some embodiments of the inventive concept, a reporting construct is provided that includes signaling components that generate a detectable signal, one or more degrons that increase the rate of intracellular digestion of associated peptide sequences, a protease cleavage site that is recognized and cleaved by a protease of interest (for example, a BoNT), and a localization sequence that localizes the intact reporting construct in a region within a cell that is relatively protected from intracellular digestion. Such components can be arranged in the following order: N-terminus:degron sequence:signaling sequence:protease substrate site:localization sequence. In some embodiments the localization sequence is part of the protease substrate site. In other embodiments the localization sequence is separate and distinct from the protease substrate site. A depiction of a typical reporting construct utilized in the characterization of a BoNT from a serotype B *Clostridium botulinum* (BoNT/B) is shown in FIG. 14. It should be appreciated that in such an embodiment the BoNT/B sensitive site can be synaptobrevin or a fragment of synaptobrevin that includes BoNT/B recognition and/or cleavage sites and a membrane localization region. While FIG. 14 depicts a construct for characterization of BoNT/B, Inventors contemplate that reporting constructs of the inventive concept can be used in cell-based or non-cell-based assays for any suitable protease and/or protease activity.

A variety of degron sequences can be utilized in reporting constructs of the inventive concept. For example, an N-terminal amino acid can be selected that increases the rate of intracellular degradation according to the N-end rule. In other embodiments of the inventive concept the degron can be selected from degron sequences of degron-containing peptide substrates, as shown in Table 1.

TABLE 1

| Degron Containing Peptides | Peptide Sequence |
| --- | --- |
| Bonger (SEQ ID NO. 11) | KTRGVEEVAEGVVLLRRRGNK |

TABLE 1-continued

| Degron Containing Peptides | Peptide Sequence |
| --- | --- |
| TAZ (SEQ ID NO. 12) | KPFLNGGPYHSREQSTDSGLGLGSYK |
| HIF-α (SEQ ID NO. 13) | ASADLDLEALAPYIPADDDFQLRK |
| iNOS (SEQ ID NO. 14) | KEEKDINNNVKKTK |
| SRC3 (SEQ ID NO. 15) | DVQKADVSSTGQGIDSK |
| Cyclin D1 (SEQ ID NO. 16) | KAAEEEESLASTPTDVRDVDIK |
| IFNAR1 (SEQ ID NO. 17) | KKYSSQTSQDSGNYSNK |
| p53 (SEQ ID NO. 18) | KPLSSSVPSQKTYQGSYGFRLGK |
| β-catenin (SEQ ID NO. 19) | KAWQQQSYLDSGIHSGATTTAPK |

Bold amino acids represent phosphorylated residues in phospho-degrons.

It should be appreciated that the localization sequence of the reporting construct can be selected to provide protection from intracellular degradation processes mediated by the N-end amino acid, for example by localizing the intact reporting construct at or near a cell membrane. Surprisingly, the inventors have found that the presence of a localizing sequence (e.g. the membrane-binding portion of synaptobrevin) can effectively prevent intracellular degradation of the intact reporting construct.

Reporting constructs of the inventive concept can utilize any suitable signaling sequence. Suitable signaling sequences include green fluorescent peptide, cyan fluorescent peptide, yellow fluorescent peptide, other green fluorescent peptide mutations, and other fluorescent peptides. In preferred embodiments two or more signaling sequences in a reporting construct are arranged such that no useful FRET (i.e. less than about 5% energy transfer) occurs between them. In other embodiments two or more fluorescent peptides can be arranged as a FRET pair within a signaling sequence. Other suitable signaling sequences include luciferase, aequorin, and other light emitting sequences. As noted above, in some embodiments of the inventive concept a second signaling sequence can be associated with or coupled to the localization sequence of the reporting construct, such that the second signaling sequence remains within the protected region of the cell following cleavage of the reporting construct. In such embodiments the second signaling sequence can be used for normalization of the signal provided by the released signaling sequence, cell numbers between different test sites or wells, and distribution of cells within a test site or well.

Signaling sequences can directly adjoin a degron sequence located at or near the N-terminus of the reporting construct. Alternatively, a signaling sequence can be separated from the degron sequence by a spacer or linker region. Such a spacer or linker can be rigid, flexible, or include both rigid and flexible regions. Such a spacer can advantageously improve the access of components of intracellular protein degradation systems by relieving steric hindrance.

Reporting constructs of the inventive concept can utilize a wide variety of intracellular protease substrate sites. Suitable intracellular protease substrate sites include caspase sensitive sites, tetanus toxin sensitive sites, BoNT sensitive sites (i.e. sites that are susceptible to cleavage by BoNT/A, BoNT/B, BoNT/C, BoNT/D, BoNT/E, BoNT/F, and/or BoNT/G), and anthrax toxin sensitive sites. In some embodiments the protease substrate site can include both protease recognition sites (i.e. sites to which the protease has an affinity) and protease cleavage sites (i.e. the specific site at which the peptide chain is cleaved). Such protease recognition sites and protease cleavage sites can be a continuous or a discontinuous sequence. In some embodiments, for example a BoNT/B sensitive reporting construct, the protease substrate site can include a localization sequence that maintains the intact reporting construct at a protected location within the cell.

Reporting constructs of the inventive concept can utilize a wide variety of localization sequences that can localize the intact reporting construct at location within the cell that is protected or partially protected from intracellular protein degradative process that are mediated by the degron sequence. Such protected sites include cell membranes, such as the interior of the plasma membrane, rough ER membrane, smooth ER membrane, vesicle membranes, and nuclear membranes. For example, a localization sequence provided by a BoNT/B protease substrate sequence can localize the intact reporting construct to a vesicle surface where it is protected or partially protected from intracellular degradative processes. In some embodiments the localization sequence can be provided as part of a protease substrate sequence. In other embodiments the localization sequence can be a distinct and separate peptide sequence that is not directly related to the protease substrate sequence. In some embodiments a localization sequence from one intracellular protease substrate sequence (for example, a BoNT/A substrate sequence) can be utilized in a reporting construct having an unrelated second intracellular protease substrate sequence (for example, a BoNT/B substrate sequence, a caspase substrate sequence, or an anthrax toxin substrate sequence).

As noted, the above described reporting constructs can be utilized in cell-based assays. In such embodiments the reporting construct can be encoded on one or more plasmids utilized to transform, either permanently or transiently, cells utilized in such assays. In a preferred embodiment such a transformed cell would express one or more types of surface receptor that provides specific uptake of an analyte in culture media. Such an analyte could trigger production of the intracellular protease to be characterized or, alternatively can include the intracellular protease to be analyzed (for example, BoNTs). Such cells can be tumor derived or otherwise immortalized to provide cell lines suitable for use in cell-based assays. Alternatively, reporting constructs can be introduced into cells that do not encode for them by physical and/or chemical means, such as ultrasound, electroporation, or fusion with encapsulating vesicles. In a preferred embodiment the cells are neuronally-derived cells that include receptors for a specified BoNT neurotoxin, and that have been transformed to express a reporting construct that includes a corresponding BoNT substrate site.

Another embodiment of the inventive concept is a cell-based assay for protease activity. Such protease activity can be a result of the activity of an analyte after it is internalized by a cell, or can be associated with a protease that is produced by the cell in response to the presence of an analyte or another environmental condition. In such a cell-based assay one or more cells that include a reporting construct of the inventive concept are provided. Such cells are exposed to a culture medium, sample, and/or environmental condition that includes the analyte to be characterized. The cells can be observed for signal originating from the reporting construct prior to or immediately following exposure to the analyte in order to obtain a baseline signal. Following exposure to the analyte the cell or cells are monitored and additional signal data from the reporting construct obtained. Such monitoring can be continuous, intermittent, or include only a single observation that follows a defined time period. Comparison of the post-exposure to signal to the baseline signal can be used to characterize amount, activity, and/or other properties of the analyte. For example, exposure of a series of test sites containing suitable cells and exposed to a series of samples containing known concentrations of the analyte of interest can be used to derive a dose/response curve, which can subsequently be used to estimate concentration of the analyte in an unknown sample. Such assays can have particular utility in replacing animal studies of toxicity or pharmaceutical effect.

In another embodiment of the inventive concept, a population of cells susceptible to BoNT/B intoxication is genetically altered, either temporarily or permanently, to express at least one of the above described reporter constructs. Images are obtained of a field containing one or more of such cells at wavelengths corresponding to an emission wavelength of at least one of the fluorescent peptides that can be released by BoNT/B proteolytic activity, prior to the exposure of such transformed cells to BoNT/B. It should be appreciated that such cells are not generally positioned in a predetermined or ordered fashion, and can be distributed randomly or essentially randomly within the field. Such imaging takes place while illuminating the field at the excitation wavelength of the fluorescent peptide and recording the image at the emission wavelength of the fluorescing peptide. In embodiments where a fluorescent peptide is present that is not released by BoNT/B activity an additional image can be obtained while illuminating the field at the corresponding excitation wavelength and recording the image at the corresponding emission wavelength of this fluorescent peptide. Following the application of sample containing (or thought to contain) BoNT/B to the cells the same field is re-imaged at least once after a suitable time interval. Image recognition software is then applied to the image recorded prior to BoNT/B application to identify regions of the image that do show useful fluorescence (e.g. cell-free regions, cells that do not express a reporting construct) and to identify regions that exceed a pre-defined signal threshold (for example, a value representing CCD saturation and/or nonlinearity). Upon exclusion of such portions of the image the remaining regions represent a quantitation mask. This quantitation mask is applied to subsequent images obtained following exposure of the field to BoNT/B. In this fashion data is selectively obtained only from cells expressing the reporting construct at the desired level or within a desired range. Such selective collection of data from relevant portions of the test area can reduce interference from scatter and background fluorescence, and advantageously reduce variation and/or improve sensitivity.

A self-correcting intensity value can be obtained from images processed in this fashion by combining pixel intensity values with the total area included within the quantitation mask. For example, average pixel intensity throughout the quantitation mask can be multiplied by the area of the quantitation mask to derive a fluorescence intensity for that image. Fluorescence intensity values obtained from a given field after exposure to BoNT/B can be compared to fluorescence intensity values obtained prior to exposure to BoNT/B, and the result used to accurately estimate the effect of BoNT/B on the distribution and/or degradation of a fluorescent peptide released from the reporting construct by BoNT/B activity. Such values can be further normalized through the use of similar measurements obtained from fluorescent peptides that are not released by BoNT/B activity. Such an embodiment can be used in methods for quantifying or otherwise characterizing BoNT/B activity, for example by comparing results obtained from an unknown sample to results obtained from a set of samples containing known amounts of BoNT/B.

Alternatively, such a method can be used to identify cell lines and/or constructs that are suitably responsive to BoNT/B, with subsequent characterization of BoNT/B being carried out by methods that use such cell lines and/or constructs and acquire data using a conventional, non-imaging fluorometer. It should be appreciated that such a characterization method is generally applicable to cell-based assays and other assays where results are variable and localized to specific areas (which may or may not be randomly positioned within an observed field) within an image, and is not restricted to use with cells and/or BoNT/B. It should also be appreciated that such a characterization method can be effectively applied when only a portion of the potential test sites (for example, cells) are functional within the proscribed test parameters. For example, a characterization method of the inventive concept can be applied to a field containing transformed cells that express a reporting construct, where less than 90%, less than 80%, less than 70%, less than 60%, less than 50%, less than 40%, less than 30%, less than 20%, or less than 10% of the cells in the field express the reporting construct at levels that are suitable for use in an assay.

In some embodiments of the inventive concept, a quantitation mask-based imaging method as described above can be used as a primary assay. In other embodiments of the inventive concept such a quantitation-mask based imaging method can be used to identify populations of cells, cell types, reporting construct configurations, or combination thereof that produce an acceptable result. Once identified such optimized cell-based reagents can be used as the basis of a non-imaging method where fluorescence data is gathered using a conventional (e.g. microwell plate) fluorometer that does not have imaging capability, but rather quantifies total fluorescence of a testing region.

EXAMPLES

A series of reporting peptide construct pairs were prepared, where each reporting peptide construct included a synaptobrevin (Vamp2) portion coupled to the carboxyl terminus of either a YFP peptide or a CFP peptide. This arrangement is shown schematically in FIG. 15A. Variations on this basic architecture inserted a degron sequence into a peptide sequence coupled to the N terminus of the YFP peptide (see FIG. 15B) to generate a series of degron-containing reporting constructs. Designations and degron content of the YFP-bearing constructs are shown in Table 2. The YFP constructs were paired with a common CFP-bearing construct (SEQ ID NO. 21) that did not include a degron sequence to provide the reporting peptide construct pairs. In this example the CFP-bearing construct (SEQ ID NO. 21) includes point mutations that prevent cleavage by BoNT/B (e.g. D64N, D65N, D68N, Q76V) while preserving the majority of the VAMP2 sequence and structure. As a result the CFP portion of the CFP-bearing construct remains localized in transformed cells and is not degraded at an accelerated rate following exposure to BoNT/B activity.

TABLE 2

| Degron Sequence | Designation |
|---|---|
| None (Control) | pMD0185 (SEQ ID NO. 20) |
| Bonger | pMD0189 (SEQ ID NO. 11; SEQ ID NO. 22) |
| iNOS | pMD0190 (SEQ ID NO. 23) |
| p53 | pMD0191 (SEQ ID NO. 9) |
| SNAP-25 | pMD0192 (SEQ ID NO. 10) |

Neuro2A (neuroblastoma) cells were seeded in EMEM+10% FBS at $2.0\times10^4$ cells per well in 96 well poly D-lysine coated tissue culture plates. The cells were allowed to recover for 18 (±2) hours. Cells were then washed with 100 μL serum-free EMEM following by a 30 minute incubation in serum-free EMEM (100 μL per well). Transfection reagents were prepared by preparing two 1.5 mL Eppendorf tubes as follows: Tube A—0.5 mL serum-free EMEM and 2.8 mg of plasmid DNA; Tube B— 0.5 mL serum-free EMEM and 7.0 μL of lipofectamine 2000™ (Life Technologies). Tubes A and B were incubated at room temperature for 5 minutes, then mixed with one another incubated for an additional 20 minutes. 25 μL of this transfection mixture was added to a well containing cells in order to provide a transient transfection.

Cells were incubated with the transfecting DNA for 18 hours, then treated with BoNT/B for 48 hours. Cells were imaged using a GE InCell™ automated cell imager at 10λ objective using brightfield, YFP, and CFP filter sets. Following this imaging the plates were washed with PBS in an automated plate washer and fluorophore emission intensities characterized using a Tecan F500™ plate reader.

FIG. 16A shows a photomicrograph of cells expressing the control (i.e. no degron sequence) reporting construct in the presence and absence of BoNT/B. Emissions from YFP and CFP fluorescent peptides are shown. In the absence of BoNT/B, YFP emission is localized in vesicles. In the presence of BoNT/B YFP emissions are re-localized, with diffusion of a YFP-containing peptide apparent throughout the cell. Localization of the CFP containing construct does not change due to the presence of point mutations that prevent cleavage by BoNT/B activity. FIG. 16B shows overall fluorescence emission from such cells as characterized using a fluorescence plate reader. Non-transfected cells were also characterized. As shown, YFP emission is sharply reduced in transformed cells exposed to BoNT/B, whereas CFP emission is relatively unaffected (the means of individual measurements at different BoNT/B concentrations falling within the variation of those measurements). As a result the results of YFP emission to CFP emission ratios parallel those of YFP emission.

FIGS. 17A to 17C show the results of fluorescence measurements made from non-transformed cells, cells transformed to express a control (i.e. not containing degron) reporting construct pair, and cells transformed to express reporting construct pairs in which the YFP-bearing construct included a degron sequence positioned towards the N-terminus relative to the YFP peptide. FIG. 17A shows the results of measurements of YFP emission in the presence and absence of BoNT/B. FIG. 17B shows the results of measurements of CFP emission in the presence and absence of BoNT/B. FIG. 17C shows the results of measurements of YFP fluorescence:CFP fluorescence ratio in the presence and absence of BoNT/B. Results are summarized below in Table 3. It is apparent that inclusion of degron sequences (e.g. iNOS and/or p53 degron sequences) positioned N-terminally from the YFP portion of the YFP-bearing member of the reporting construct pair can provide improved dynamic range in a BoNT/B cell-based assay, relative to cells transformed using an analogous construct pair lacking the degron sequence.

TABLE 3

| Construct | Vehicle Only (YFP:CFP ratio) | 100 nM BoNT/B (YFP:CFP ratio) | Dynamic Range |
|---|---|---|---|
| pMD0185 (no degron) | 3.90 | 1.78 | 2.20 |
| pMD0189 (Bonger) | 1.82 | 1.04 | 1.75 |
| pMD0190 (iNOS) | 2.17 | 0.74 | 2.93 |
| pMD0191 (p53) | 3.63 | 0.89 | 4.09 |

Dynamic Range = (YFP:CFP emission ratio with vehicle-only) ÷ (YFP:CFP emission ratio with vehicle + 100 nm BoNT/B)

Figure 18A:
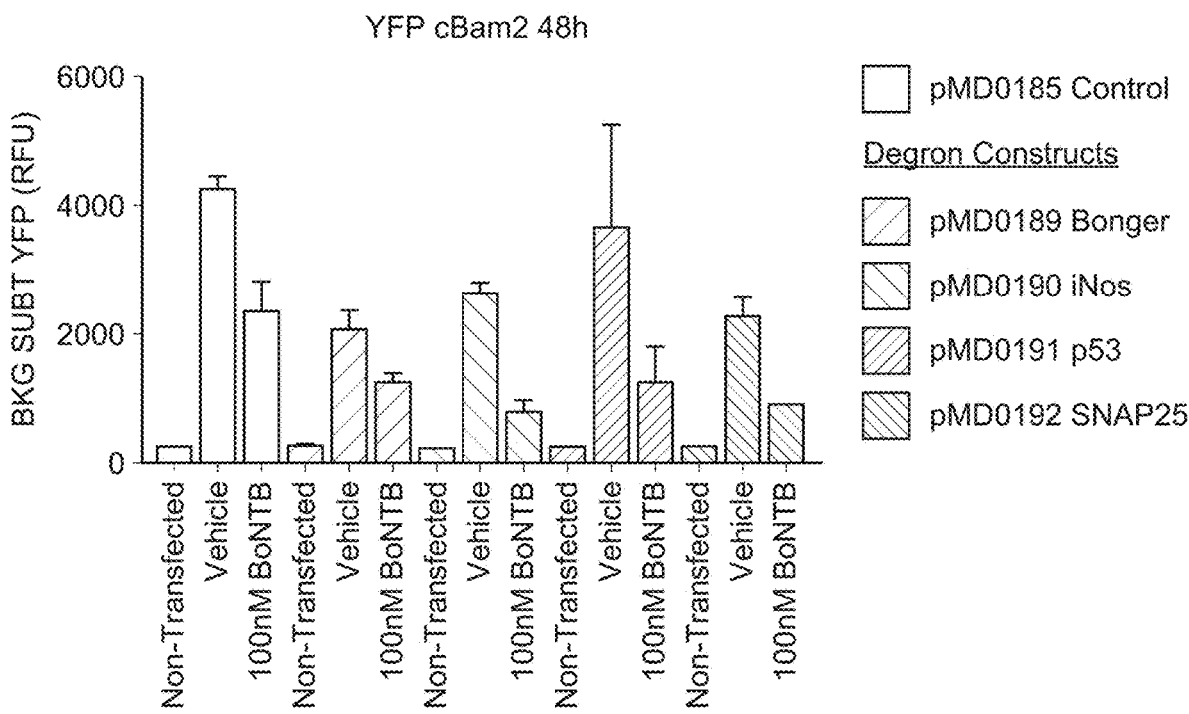
FIGS. 18A to 18C shows results of studies similar to those of FIG. 17A to 17C, incorporating an additional cell population transformed to express a reporting construct pair with a degron sequence obtained from SNAP-25.
Figure 18B:
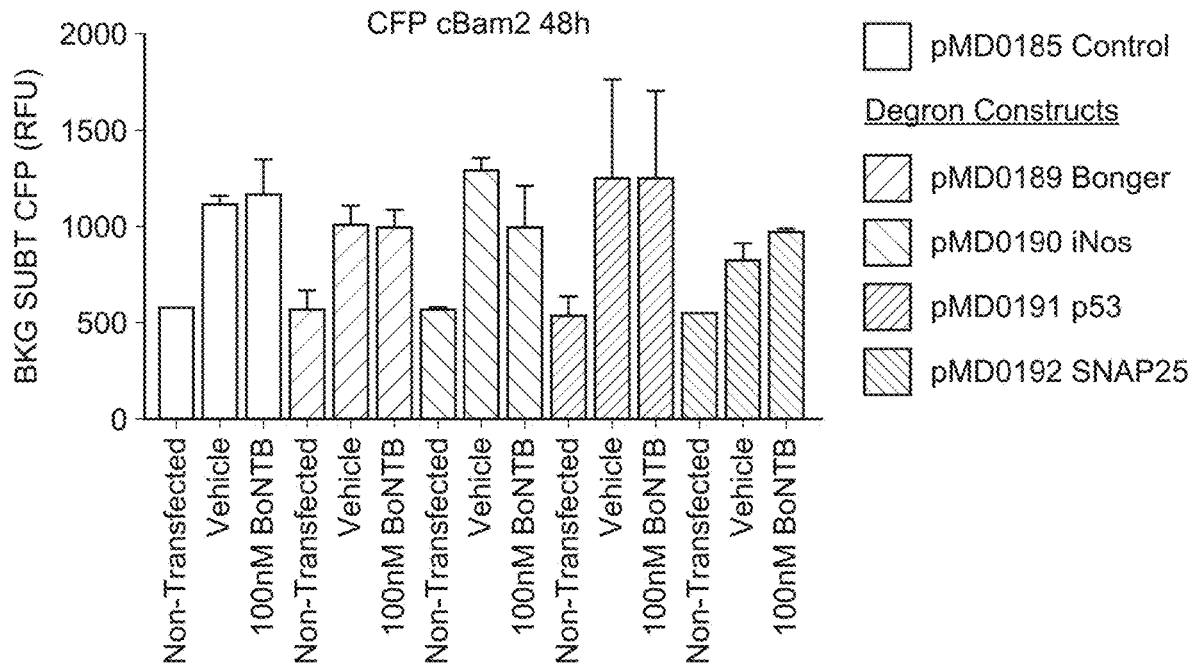
Figure 18C:
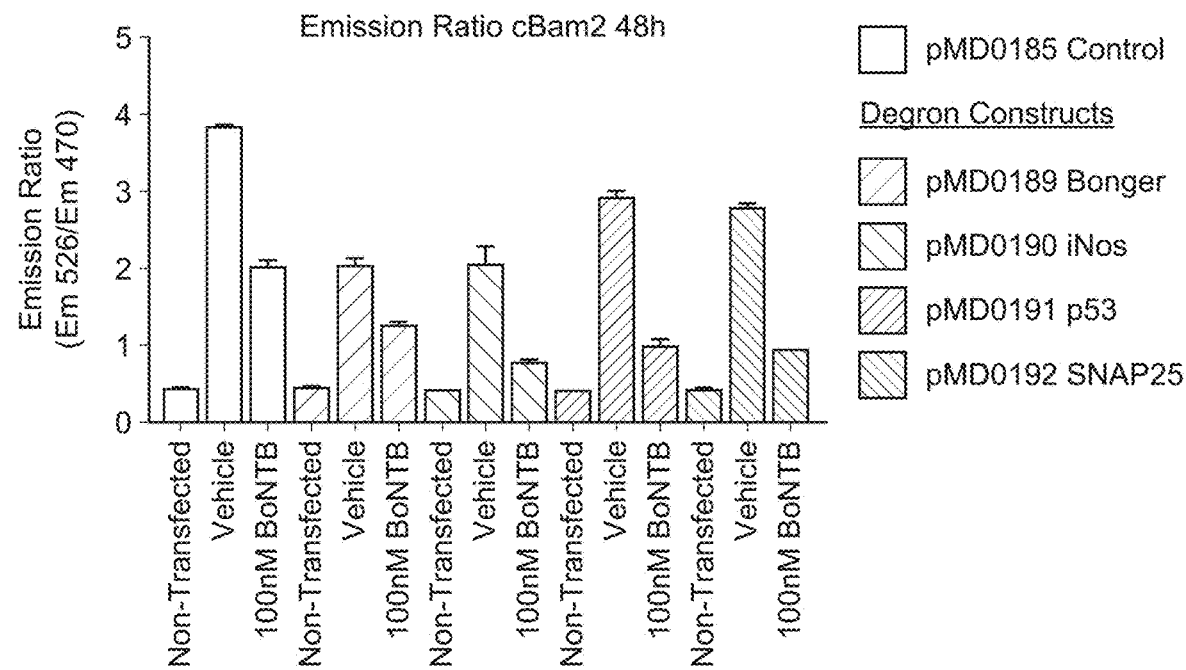

FIGS. 18A to 18C show the results of similar studies performed using an additional set of cells transformed using a reporting construct pair that incorporates a degron sequence from SNAP-25 positioned towards the N-terminus relative to the YFP peptide. FIG. 18A shows the results of measurements of YFP emission in the presence and absence of BoNT/B. FIG. 18B shows the results of measurements of CFP emission in the presence and absence of BoNT/B. FIG. 18C shows the results of measurements of YFP fluorescence:CFP fluorescence ratio in the presence and absence of BoNT/B. Results are summarized below in Table 4. It is apparent that inclusion of degron sequences (e.g. iNOS, p53, and/or SNAP-25 degron sequences) positioned N-terminally from the YFP portion of the YFP-bearing member of the reporting construct pair can provide improved dynamic range in a BoNT/B cell-based assay, relative to cells transformed using an analogous construct pair lacking the degron sequence.

TABLE 4

| Construct | Vehicle Only (YFP:CFP ratio) | 100 nM BoNT/B (YFP:CFP ratio) | Dynamic Range |
|---|---|---|---|
| pMD0185 (no degron) | 3.80 | 1.99 | 1.91 |
| pMD0189 (Bonger) | 2.02 | 1.23 | 1.64 |
| pMD0190 (iNOS) | 2.04 | 0.76 | 2.70 |
| pMD0191 (p53) | 2.90 | 0.96 | 3.01 |
| pMD0192 (SNAP-25) | 2.77 | 0.91 | 3.03 |

Dynamic Range = (YFP:CFP emission ratio with vehicle-only) ÷ (YFP:CFP emission ratio with vehicle + 100 nm BoNT/B)

Figure 19A:
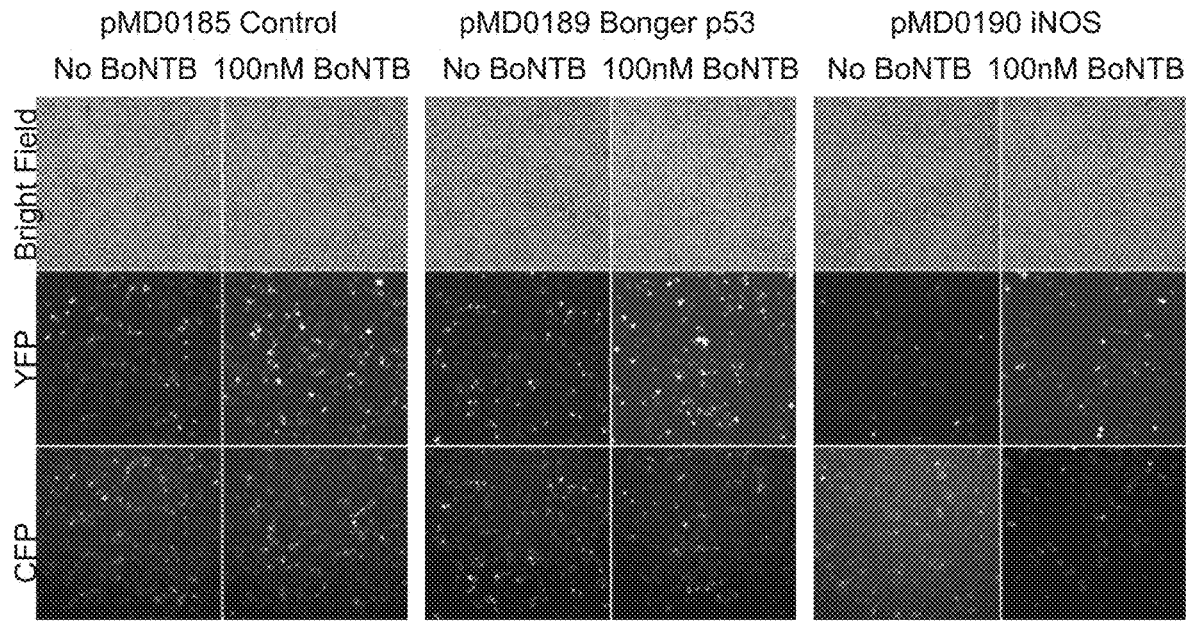
FIGS. 19A and 19B provide photomicrographs obtained from cells transformed with a control reporting construct pair that does not include a degron sequence and from cells transformed with reporting constructs that include a degron sequence.
Figure 19B:
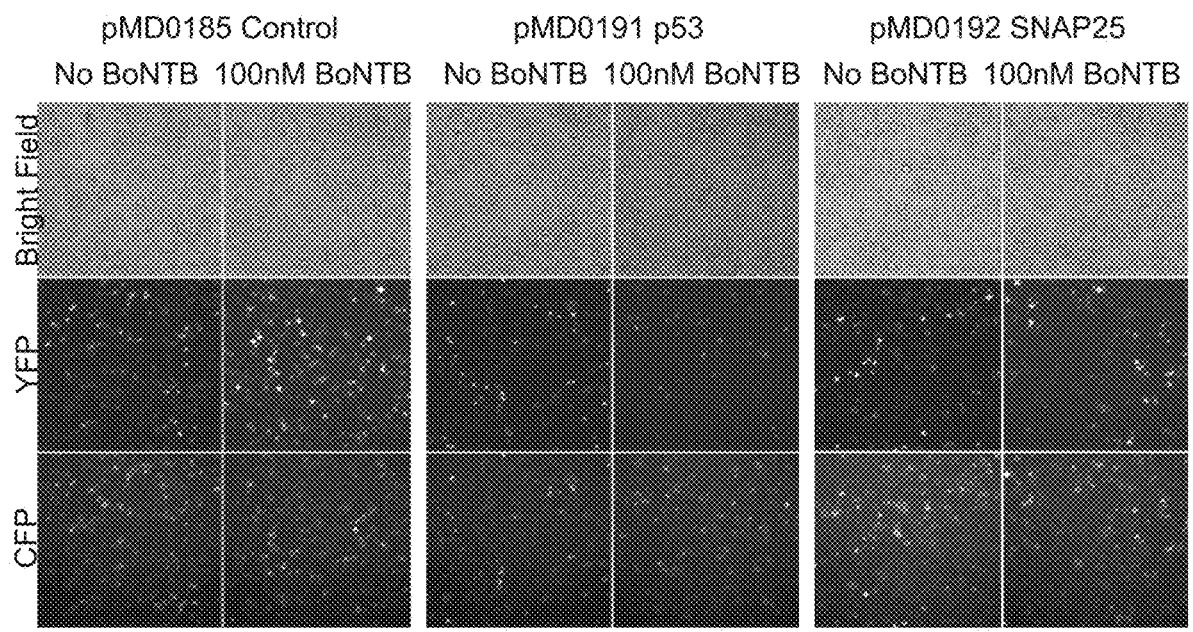

Surprisingly, Inventors have found that inclusion of a degron sequence position N-terminally to a fluorescent peptide portion of a reporting construct can modify cytosolic relocalization of the fluorescent peptide on release from the reporting construct (for example, by proteolytic activity of a botulinum neurotoxin). This is evident in the photomicrographs shown in FIGS. 19A and 19B. FIG. 19A shows brightfield, YFP emission, and CFP emission from transformed cells expressing a control reporting construct pair (containing no degron sequence) and transformed cells expressing reporting construct pairs that include degron sequences (specifically, Bonger or iNOS degron sequences) positioned N-terminally to the YFP peptide of the YFP-bearing member of the reporting construct pair. Images were taken in the presence and in the absence of BoNT/B. The cells carrying the pMD0190 constructs (which showed improved dynamic range relative to control cells on exposure to BoNT/B) showed reduced YFP fluorescence and less cytosolic relocalization of YFP-bearing peptide than control cells following exposure to BoNT/B. FIG. 12B shows the results of similar studies performed using cells carrying either the pMD0191 or pMD0192 reporting construct pairs, both of which show improved dynamic range on exposure to BoNT/B relative to control cells. The cells carrying the pMD0191 and pMD0192 constructs also showed reduced YFP fluorescence and less cytosolic relocalization of YFP-bearing peptide than control cells following exposure to BoNT/B.

Figure 20:
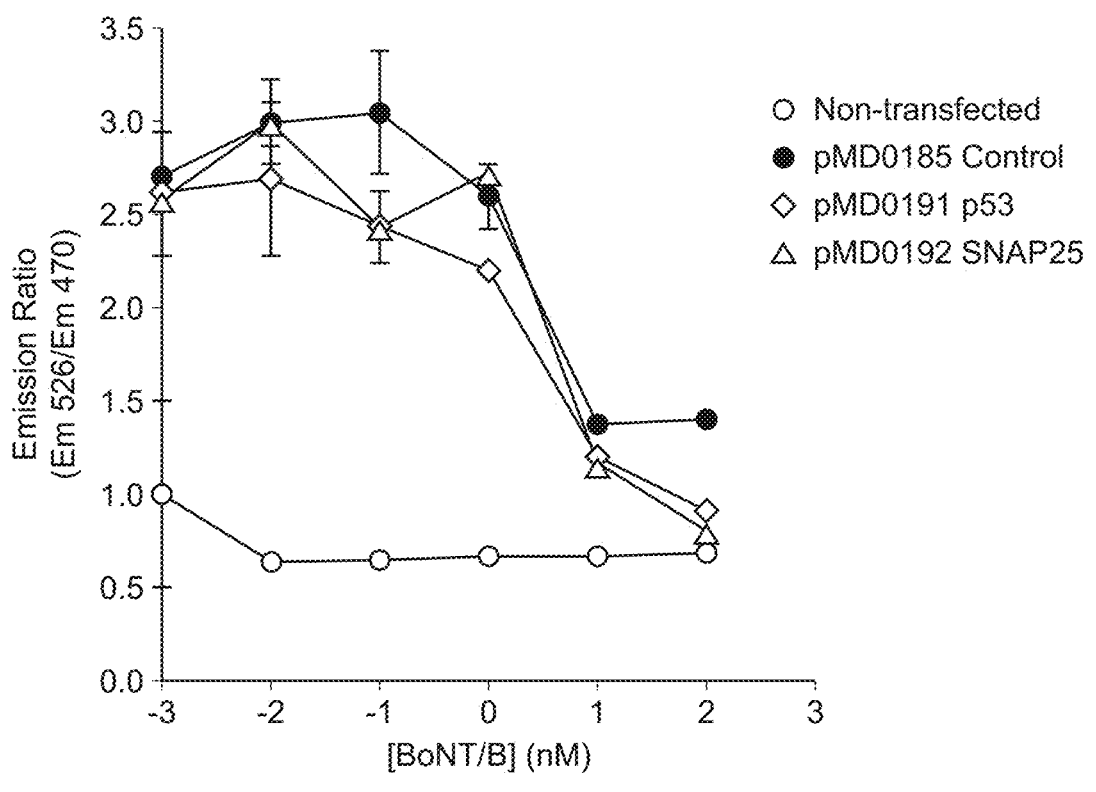

Results of application of BoNT/B at different concentrations to cells expressing a control BoNT/B-reactive construct pair lacking a degron sequence and cells expressing analogous BoNT/B-reactive construct pair where the YFP-bearing peptide includes a degron sequence are shown in FIG. 20. In such assays increasing BoNT/B concentrations are associated with a decreasing YFP emission, which results in a decreasing YFP emission:CFP emission ratio. As shown, cells expressing the control construct pair (pMD0185) reach maximum emission ratio (indicating assay saturation) at approximately 1 nM BoNT/B. Cells expressing a p53 degron-containing construct, however, do not reach assay saturation until approximately $10^{-2}$ nM BoNT/B, indicating a substantial improvement in sensitivity.

In some embodiments, methods described above can be performed manually. In other embodiments, certain aspects of a method (for example, sample and/or reagent dispensing, transportation of labware in and out of an incubator, etc.) can be performed in an automated fashion, while other aspects can be performed manually. In other embodiments a method of the inventive concept essentially all of the steps of the method can be performed in an automated fashion, for example through the use of a programmable laboratory robot.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A pair of reporting constructs for characterizing botulinum serotype neurotoxin comprising:
   a first reporter construct comprising a first membrane binding peptide configured to localize to a vesicle membrane and a first fluorescent peptide joined by a first linking peptide interposed between the first membrane binding peptide and the first fluorescent peptide, wherein the first fluorescent peptide has a first emission wavelength, and wherein the first linking peptide is derived from synaptobrevin; and
   a second reporter construct comprising a second membrane binding peptide configured to localize to the vesicle membrane and a second fluorescent peptide joined by a second linking peptide interposed between the second membrane binding peptide and the second fluorescent peptide, wherein the second fluorescent peptide has a second emission wavelength, and wherein the second linking peptide is derived from synaptobrevin,
   wherein the first fluorescent peptide and the second fluorescent peptide are positioned such that less than 5% Forster resonance energy transfer (FRET) occurs between them when the first reporting construct and the second reporting construct are co-located on a membrane surface of the vesicle, and
   wherein the first fluorescent peptide comprises one or more first mutations that increase the rate of intracellular proteolysis relative to an analogous fluorescent peptide that does not incorporate the one or more first mutations.

2. The pair of reporting constructs of claim 1, wherein the second linking peptide comprises one or more second mutations that decrease susceptibility to proteolysis by botulinum B neurotoxin relative to an analogous linking peptide that does not comprise said one or more second mutations.

3. The pair of reporting constructs of claim 2, wherein at least one of the one or more second mutations is a point mutation of an amino acid that forms part of a botulinum serotype B neurotoxin cleavage site of synaptobrevin.

4. The pair of reporting constructs of claim 2, wherein at least one of the one or more second mutations is a point mutation of an amino acid that forms part of an exosite of synaptobrevin that interacts with botulinum serotype B neurotoxin.

5. The pair of reporting constructs of claim 2, wherein at least one of the one or more second mutations is a point mutation selected from the group consisting of D64N, D65N, D68N, and Q76V of synaptobrevin.

6. A plasmid encoding the pair of reporting constructs of claim 1.

7. A first plasmid encoding the first reporting construct of claim 1, and a second plasmid encoding the second reporting construct of claim 1.

8. The pair of reporting constructs of claim 1, wherein at least one of the first fluorescent peptide and the second fluorescent peptide are derived from green fluorescent protein or a green fluorescent protein mutation.

9. The pair of reporting constructs of claim 1, wherein the one or more mutations comprise a point mutation that replaces a native amino acid with a basic amino acid.

10. A cell expressing the pair of reporting constructs of claim 1.

11. The pair of reporting constructs of claim 10, wherein the cell is selected from the group consisting of aNeuro2A cell, an M17 cell, a PC12 cell, an SK-N-SH cell, an LNCaP cell, an immortalized murine astrocyte, an SV40T cell, a human or murine hTERT immortalized cell, a neuron derived from an induced pluripotent stem cell, a stem cell derived neuron, and a primary neuron.

* * * * *

SEQUENCE LISTING

<160> NUMBER OF SEQ ID NOS: 23

<210> SEQ ID NO 1
<211> LENGTH: 1077
<212> TYPE: DNA
<213> ORGANISM: Artificial Sequence
<220> FEATURE:
<223> OTHER INFORMATION: pMD0032 YFPVAMP2, plasmid encoding for YFPVAMP2 construct

<400> SEQUENCE: 1

```
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccttcggcta cggcctgcag tgcttcgccc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagct accagtccgc cctgagcaaa gaccccaacg agaagcgcga tcacatggtc    660
ctgctggagt tcgtgaccgc cgccgggatc actctcggca tggacgagct gtacaagagt    720
ggaggcatgt cggctaccgc tgccaccgtc ccgcctgccg cccggccgg cgagggtggc    780
cccctgcac ctcctccaaa tcttaccagt aacaggagac tgcagcagac ccaggcccag    840
gtggatgagg tggtggacat catgagggtg aatgtggaca aggtcctgga gcgrgaccag    900
aagctatcgg aactggatga tcgcgcagat gccctccagg cagggcctc ccagtttgaa    960
acaagtgcag ccaagctcaa gcgcaaatac tggtggaaaa acctcaagat gatgatcatc   1020
ttgggagtga tttgcgccat catcctcatc atcatcatcg tttacttcag cacttaa     1077
```

<210> SEQ ID NO 2
<211> LENGTH: 1077
<212> TYPE: DNA
<213> ORGANISM: Artificial Sequence
<220> FEATURE:
<223> OTHER INFORMATION: pMD0034 ECFPVAMP, plasmid encoding for ECFPVAMP2 construct

<400> SEQUENCE: 2

```
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccctgacctg gggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacat cagccacaac gtctatatca ccgccgacaa gcagaagaac    480
ggcatcaagg ccaacttcaa gatccgccac aacatcgagg acggcagcgt gcagctcgcc    540
gaccactacc agcagaacac ccccatcggc gacggccccg tgctgctgcc cgacaaccac    600
```

```
tacctgagca cccagtccgc cctgagcaaa gaccccaacg agaagcgcga tcacatggtc    660
ctgctggagt tcgtgaccgc cgccgggatc actctcggca tggacgagct gtacaagagt    720
ggaggcatgt cggctaccgc tgccaccgtc ccgcctgccg cccggccgg cgagggtggc     780 cccctgcac ctcctccaaa tcttaccagt aacaggagac tgcagcagac ccaggcccag     840
gtggatgagg tggtggacat catgagggtg aatgtggaca aggtcctgga gcgrgaccag    900
aagctatcgg aactggatga tcgcgcagat gccctccagg caggggcctc ccagtttgaa    960
acaagtgcag ccaagctcaa gcgcaaatac tggtggaaaa acctcaagat gatgatcatc   1020
ttgggagtga tttgcgccat catcctcatc atcatcatcg tttacttcag cacttaa      1077
```

<210> SEQ ID NO 3
<211> LENGTH: 1076
<212> TYPE: DNA
<213> ORGANISM: Artificial Sequence
<220> FEATURE:
<223> OTHER INFORMATION: pMD0034 YFPVAMP2, plasmid encoding for YFPVAMP2
      construct

<400> SEQUENCE: 3

```
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccttcggcta cggcctgcag tgcttcgccc gctacccga ccacatgaag     240 cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagct accagtccgc cctgagcaaa gaccccaacg agaagcgcga tcacatggtc    660
ctgctggagt tcgtgaccgc cgccgggatc actctcggca tggacgagct gtacaagagt    720
ggaggcatgt cggctaccgc tgccaccgtc ccgcctgccg cccggccgg cgagggtggc     780 cccctgcacc tcctccaaat cttaccagta acaggagact gcagcagacc caggcccagg    840 tgatgaggt ggtggacatc atgagggtga atgtggacaa ggtcctggag cgrgaccaga    900
agctatcgga actggatgat cgcgcagatg ccctccaggc aggggcctcc cagtttgaaa    960
caagtgcagc caagctcaag cgcaaatact ggtggaaaaa cctcaagatg atgatcatct   1020
tgggagtgat ttgcgccatc atcctcatca tcatcatcgt ttacttcagc acttaa       1076
```

<210> SEQ ID NO 4
<211> LENGTH: 1077
<212> TYPE: DNA
<213> ORGANISM: Artificial Sequence
<220> FEATURE:
<223> OTHER INFORMATION: pMD0071 ECFPVAMP2, plasmid encoding for
      ECFPVAMP2 construct

<400> SEQUENCE: 4

```
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
```

```
ggcaagctga ccctgaagtt catctgcacc accggcaagc tgcccgtgcc ctggcccacc      180
ctcgtgacca ccctgacctg gggcgtgcag tgcttcagcc gctaccccga ccacatgaag      240
cagcacgact tcttcaagtc cgccatgccc gaaggctacg tccaggagcg caccatcttc      300
ttcaaggacg acggcaacta caagacccgc gccgaggtga agttcgaggg cgacaccctg      360
gtgaaccgca tcgagctgaa gggcatcgac ttcaaggagg acggcaacat cctggggcac      420
aagctggagt acaactacat cagccacaac gtctatatca ccgccgacaa gcagaagaac      480
ggcatcaagg ccaacttcaa gatccgccac aacatcgagg acggcagcgt gcagctcgcc      540
gaccactacc agcagaacac ccccatcggc gacggccccg tgctgctgcc cgacaaccac      600
tacctgagca cccagtccgc cctgagcaaa gaccccaacg agaagcgcga tcacatggtc      660
ctgctggagt tcgtgaccgc cgccgggatc actctcggca tggacgagct gtacaagagt      720
ggaggcatgt cggctaccgc tgccaccgtc ccgcctgccg ccccggccgg cgagggtggc      780
cccccctgcac ctcctccaaa tcttaccagt aacaggagac tgcagcagac ccaggcccag      840
gtggatgagg tggtggacat catgagggtg aatgtgacaa ggtcctgga gcgrgaccag       900
aagctatcgg aactggatga tcgcgcagat gccctccagg caggggcctc cgtgtttgaa      960
acaagtgcag ccaagctcaa gcgcaaatac tggtggaaaa acctcaagat gatgatcatc     1020
ttgggagtga tttgcgccat catcctcatc atcatcatcg tttacttcag cacttaa        1077
```

<210> SEQ ID NO 5  
<211> LENGTH: 1077  
<212> TYPE: DNA  
<213> ORGANISM: Artificial Sequence  
<220> FEATURE:  
<223> OTHER INFORMATION: pMD0071 YFPVAMP2, plasmid encoding for YFPVAMP2 construct

<400> SEQUENCE: 5

```
atggtgagca agggcgagga gctgttcacc ggggtggtgc ccatcctggt cgagctggac       60
ggcgacgtaa acggccacaa gttcagcgtg tccggcgagg gcgagggcga tgccacctac      120
ggcaagctga ccctgaagtt catctgcacc accggcaagc tgcccgtgcc ctggcccacc      180
ctcgtgacca ccttcggcta cggcctgcag tgcttcgccc gctaccccga ccacatgaag      240
cagcacgact tcttcaagtc cgccatgccc gaaggctacg tccaggagcg caccatcttc      300
ttcaaggacg acggcaacta caagacccgc gccgaggtga agttcgaggg cgacaccctg      360
gtgaaccgca tcgagctgaa gggcatcgac ttcaaggagg acggcaacat cctggggcac      420
aagctggagt acaactacaa cagccacaac gtctatatca tggccgacaa gcagaagaac      480
ggcatcaagg tgaacttcaa gatccgccac aacatcgagg acggcagcgt gcagctcgcc      540
gaccactacc agcagaacac ccccatcggc gacggccccg tgctgctgcc cgacaaccac      600
tacctgagct accagtccgc cctgagcaaa gaccccaacg agaagcgcga tcacatggtc      660
ctgctggagt tcgtgaccgc cgccgggatc actctcggca tggacgagct gtacaagagt      720
ggaggcatgt cggctaccgc tgccaccgtc ccgcctgccg ccccggccgg cgagggtggc      780
cccccctgcac ctcctccaaa tcttaccagt aacaggagac tgcagcagac ccaggcccag      840
gtggatgagg tggtggacat catgagggtg aatgtgacaa ggtcctgga gcgrgaccag       900
aagctatcgg aactggatga tcgcgcagat gccctccagg caggggcctc cgtgtttgaa      960
acaagtgcag ccaagctcaa gcgcaaatac tggtggaaaa acctcaagat gatgatcatc     1020
ttgggagtga tttgcgccat catcctcatc atcatcatcg tttacttcag cacttaa        1077
```

<210> SEQ ID NO 6
<211> LENGTH: 1077
<212> TYPE: DNA
<213> ORGANISM: Artificial Sequence
<220> FEATURE:
<223> OTHER INFORMATION: pMD0185 ECFPVAMP2, plasmid encoding for ECFPVAMP2 construct

<400> SEQUENCE: 6

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgacctg gggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacat cagccacaac gtctatatca ccgccgacaa gcagaagaac     480
ggcatcaagg ccaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagagt     720
ggaggcatgt cggctaccgc tgccaccgtc ccgcctgccg cccggccgg cgagggtggc     780
cccctgcac ctcctccaaa tcttaccagt aacaggagac tgcagcagac ccaggcccag     840
gtggatgagg tggtggacat catgagggtg aatgtggaca aggtcctgga gcgrgaccag     900
aagctatcgg aactgaataa tcgcgcaaat gccctccagg caggggcctc cgtgttgaa     960
acaagtgcag ccaagctcaa gcgcaaatac tggtggaaaa acctcaagat gatgatcatc    1020
ttgggagtga tttgcgccat catcctcatc atcatcatcg tttacttcag cacttaa       1077
```

<210> SEQ ID NO 7
<211> LENGTH: 843
<212> TYPE: DNA
<213> ORGANISM: Artificial Sequence
<220> FEATURE:
<223> OTHER INFORMATION: pMD0185 YFPVAMP2, plasmid encoding for YFPVAMP2 construct

<400> SEQUENCE: 7

```
atgaagcagc acgacttctt caagtccgcc atgcccgaag gctacgtcca ggagcgcacc      60
atcttcttca aggacgacgg caactacaag acccgcgccg aggtgaagtt cgagggcgac     120
accctggtga accgcatcga gctgaagggc atcgacttca aggaggacgg caacatcctg     180
ggcacaagc tggagtacaa ctacaacagc cacaacgtct atatcatggc cgacaagcag     240
aagaacggca tcaaggtgaa cttcaagatc cgccacaaca tcgaggacgg cagcgtgcag     300
ctcgccgacc actaccagca gaacaccccc atcggcgacg gccccgtgct gctgcccgac     360
aaccactacc tgagctacca gtccgccctg agcaaagacc ccaacgagaa gcgcgatcac     420
atggtcctgc tggagttcgt gaccgccgcc gggatcactc tcggcatgga cgagctgtac     480
aagagtggag gcatgtcggc taccgctgcc accgtcccgc ctgccgcccc ggccggcgag     540
ggtggccccc ctgcacctcc tccaaatctt accagtaaca ggagactgca gcagacccag     600
gcccaggtgg atgaggtggt ggacatcatg agggtgaatg tggacaaggt cctggagcgr     660
```

| | |
|---|---|
| gaccagaagc tatcggaact ggatgatcgc gcagatgccc tccaggcagg ggcctcccag | 720 |
| tttgaaacaa gtgcagccaa gctcaagcgc aaatactggt ggaaaaacct caagatgatg | 780 |
| atcatcttgg gagtgatttg cgccatcatc ctcatcatca tcatcgttta cttcagcact | 840 |
| taa | 843 |

<210> SEQ ID NO 8
<211> LENGTH: 1812
<212> TYPE: DNA
<213> ORGANISM: Artificial Sequence
<220> FEATURE:
<223> OTHER INFORMATION: pMD0183 YFPYFPVAMP2, encoding a construct containing two YFP sequences

<400> SEQUENCE: 8

| | |
|---|---|
| atggtgagca agggcgagga gctgttcacc ggggtggtgc ccatcctggt cgagctggac | 60 |
| ggcgacgtaa acggccacaa gttcagcgtg tccggcgagg gcgagggcga tgccacctac | 120 |
| ggcaagctga ccctgaagtt catctgcacc accggcaagc tgcccgtgcc ctggcccacc | 180 |
| ctcgtgacca ccttcggcta cggcctgcag tgcttcgccc gctaccccga ccacatgaag | 240 |
| cagcacgact tcttcaagtc cgccatgccc gaaggctacg tccaggagcg caccatcttc | 300 |
| ttcaaggacg acggcaacta caagacccgc gccgaggtga agttcgaggg cgacaccctg | 360 |
| gtgaaccgca tcgagctgaa gggcatcgac ttcaaggagg acggcaacat cctgggcac | 420 |
| aagctggagt acaactacaa cagccacaac gtctatatca tggccgacaa gcagaagaac | 480 |
| ggcatcaagg tgaacttcaa gatccgccac aacatcgagg acggcagcgt gcagctcgcc | 540 |
| gaccactacc agcagaacac ccccatcggc gacggccccg tgctgctgcc cgacaaccac | 600 |
| tacctgagct accagtccgc cctgagcaaa gaccccaacg agaagcgcga tcacatggtc | 660 |
| ctgctggagt tcgtgaccgc cgccgggatc actctcggca tggacgagct gtacaagtct | 720 |
| ggaggcaagc ttgcaatggt gagcaagggc gaggagctgt tcaccggggt ggtgcccatc | 780 |
| ctggtcgagc tggacggcga cgtaaacggc cacaagttca gcgtgtccgg cgagggcgag | 840 |
| ggcgatgcca cctacggcaa gctgaccctg aagttcatct gcaccaccgg caagctgccc | 900 |
| gtgccctggc ccaccctcgt gaccaccttc ggctacggcc tgcagtgctt cgcccgctac | 960 |
| cccgaccaca tgaagcagca cgacttcttc aagtccgcca tgcccgaagg ctacgtccag | 1020 |
| gagcgcacca tcttcttcaa ggacgacggc aactacaaga cccgcgccga ggtgaagttc | 1080 |
| gagggcgaca ccctggtgaa ccgcatcgag ctgaagggca tcgacttcaa ggaggacggc | 1140 |
| aacatcctgg gcacaagct ggagtacaac tacaacagcc acaacgtcta tatcatggcc | 1200 |
| gacaagcaga gaacggcat caaggtgaac ttcaagatcc gccacaacat cgaggacggc | 1260 |
| agcgtgcagc tcgccgacca ctaccagcag aacacccca tcggcgacgg ccccgtgctg | 1320 |
| ctgcccgaca accactacct gagctaccag tccgccctga gcaaagaccc caacgagaag | 1380 |
| cgcgatcaca tggtcctgct ggagttcgtg accgccgccg ggatcactct cggcatggac | 1440 |
| gagctgtaca agagtggagg catgtcggct accgctgcca ccgtcccgcc tgccgccccg | 1500 |
| gccggcgagg gtggcccccc tgcacctcct ccaaatctta ccagtaacag agactgcagg | 1560 |
| cagacccagg cccaggtgga tgaggtggtg acatcatga gggtgaatgt ggacaaggtc | 1620 |
| ctggagcgag accagaagct atcggaactg atgatcgcg cagatgccct ccaggcaggg | 1680 |
| gcctcccagt ttgaaacaag tgcagccaag ctcaagcgca aatactggtg gaaaaacctc | 1740 |
| aagatgatga tcatcttggg agtgatttgc gccatcatcc tcatcatcat catcgtttac | 1800 |

-continued ttcagcactt aa    1812

<210> SEQ ID NO 9
<211> LENGTH: 1116
<212> TYPE: DNA
<213> ORGANISM: Artificial Sequence
<220> FEATURE:
<223> OTHER INFORMATION: pMD0191, plasmid encoding a YFP-bearing
      construct that includes a p53 degron sequence

<400> SEQUENCE: 9

| | |
|---|---|
| atgggcaaag gttcctacgg ttccggtggc aagcttgcaa tggtgagcaa gggcgaggag | 60 |
| ctgttcaccg gggtggtgcc catcctggtc gagctggacg gcgacgtaaa cggccacaag | 120 |
| ttcagcgtgt ccggcgaggg cgagggcgat gccacctacg gcaagctgac cctgaagttc | 180 |
| atctgcacca ccggcaagct gcccgtgccc tggcccaccc tcgtgaccac cttcggctac | 240 |
| ggcctgcagt gcttcgcccg ctaccccgac cacatgaagc agcacgactt cttcaagtcc | 300 |
| gccatgcccg aaggctacgt ccaggagcgc accatcttct tcaaggacga cggcaactac | 360 |
| aagacccgcg ccgaggtgaa gttcgagggc gacaccctgg tgaaccgcat cgagctgaag | 420 |
| ggcatcgact tcaaggagga cggcaacatc ctggggcaca gctggagta caactacaac | 480 |
| agccacaacg tctatatcat ggccgacaag cagaagaacg gcatcaaggt gaacttcaag | 540 |
| atccgccaca acatcgagga cggcagcgtg cagctcgccg accactacca gcagaacacc | 600 |
| cccatcggcg acggccccgt gctgctgccc gacaaccact acctgagcta ccagtccgcc | 660 |
| ctgagcaaag accccaacga gaagcgcgat cacatggtcc tgctggagtt cgtgaccgcc | 720 |
| gccgggatca ctctcggcat ggacgagctg tacaagagtg gaggcatgtc ggctaccgct | 780 |
| gccaccgtcc cgcctgccgc cccggccggc gagggtggcc cccctgcacc tcctccaaat | 840 |
| cttaccagta acaggagact gcagcagacc caggcccagg tggatgaggt ggtggacatc | 900 |
| atgagggtga atgtggacaa ggtcctggag cgagaccaga agctatcgga actggatgat | 960 |
| cgcgcagatg ccctccaggc aggggcctcc cagtttgaaa caagtgcagc caagctcaag | 1020 |
| cgcaaatact ggtggaaaaa cctcaagatg atgatcatct gggagtgat ttgcgccatc | 1080 |
| atcctcatca tcatcatcgt ttacttcagc acttaa | 1116 |

<210> SEQ ID NO 10
<211> LENGTH: 1013
<212> TYPE: DNA
<213> ORGANISM: Artificial Sequence
<220> FEATURE:
<223> OTHER INFORMATION: MD0192, plasmid encoding a YFP-bearing
      construct including a SNAP-25 degron sequence

<400> SEQUENCE: 10

| | |
|---|---|
| atgggccgtg caacaaagat gctgggaagt ggttcgaatt ctggtggttc taagcttgca | 60 |
| atggtgagca aggggcgagga gctgttcacc ggggtggtgc ccatcctggt cgagctggac | 120 |
| ggcgacgtaa acggccacaa gttcagcgtg tccggcgagg gcgagggcga tgccacctac | 180 |
| ggcaagctga ccctgaagtt catctgcacc accggcaagc tgcccgtgcc ctggcccacc | 240 |
| ctcgtgacca ccttcggcta cggcctgcag tgcttcgccc gctaccccga ccacatgaag | 300 |
| cagcacgact tcttcaagtc cgccatgccc gaaggctacg tccaggagcg caccatcttc | 360 |
| ttcaaggacg acacaacagc cacaacgtct atatcatggc cgacaagcag aagaacggca | 420 |
| tcaaggtgaa cttcaagatc cgccacaaca tcgaggacgg cagcgtgcag ctcgccgacc | 480 |

```
actaccagca gaacaccccc atcggcgacg gccccgtgct gctgcccgac aaccactacc      540
tgagctacca gtccgccctg agcaaagacc ccaacgagaa gcgcgatcac atggtcctgc      600
tggagttcgt gaccgccgcc gggatcactc tcggcatgga cgagctgtac aagagtggag      660
gcatgtcggc taccgctgcc accgtcccgc ctgccgcccc ggccggcgag ggtggccccc      720
ctgcacctcc tccaaatctt accagtaaca ggagactgca gcagacccag gcccaggtgg      780
atgaggtggt ggacatcatg agggtgaatg tggacaaggt cctggagcgg gaccagaagt      840
tgtcggagct ggatgaccgt gcagatgccc tccaggcagg ggcctccag tttgaaacaa       900 gtgcagccaa gctcaagcgc aaatactggt ggaaaaacct caagatgatg atcatcttgg      960
gagtgatctg cgccatcatc ctcatcatca tcatcgttta cttcagcact taa            1013
```

<210> SEQ ID NO 11
<211> LENGTH: 21
<212> TYPE: PRT
<213> ORGANISM: Artificial Sequence
<220> FEATURE:
<223> OTHER INFORMATION: Peptide incorporating Bonger degron sequence

<400> SEQUENCE: 11

Lys Thr Arg Gly Val Glu Glu Val Ala Glu Gly Val Val Leu Leu Arg
1               5                   10                  15

Arg Arg Gly Asn Lys
            20

<210> SEQ ID NO 12
<211> LENGTH: 26
<212> TYPE: PRT
<213> ORGANISM: Artificial Sequence
<220> FEATURE:
<223> OTHER INFORMATION: Peptide incorporating TAZ degron

<400> SEQUENCE: 12

Lys Pro Phe Leu Asn Gly Gly Pro Tyr His Ser Arg Glu Gln Ser Thr
1               5                   10                  15

Asp Ser Gly Leu Gly Leu Gly Ser Tyr Lys
            20                  25

<210> SEQ ID NO 13
<211> LENGTH: 24
<212> TYPE: PRT
<213> ORGANISM: Artificial Sequence
<220> FEATURE:
<223> OTHER INFORMATION: Peptide incorporating HIF-alpha degron

<400> SEQUENCE: 13

Ala Ser Ala Asp Leu Asp Leu Glu Ala Leu Ala Pro Tyr Ile Pro Ala
1               5                   10                  15

Asp Asp Asp Phe Gln Leu Arg Lys
            20

<210> SEQ ID NO 14
<211> LENGTH: 14
<212> TYPE: PRT
<213> ORGANISM: Artificial Sequence
<220> FEATURE:
<223> OTHER INFORMATION: Peptide incorporating iNOS degron

<400> SEQUENCE: 14

Lys Glu Glu Lys Asp Ile Asn Asn Asn Val Lys Lys Thr Lys
1               5                   10

```
<210> SEQ ID NO 15
<211> LENGTH: 17
<212> TYPE: PRT
<213> ORGANISM: Artificial Sequence
<220> FEATURE:
<223> OTHER INFORMATION: Peptide incorporating SRC3 degron

<400> SEQUENCE: 15

Asp Val Gln Lys Ala Asp Val Ser Ser Thr Gly Gln Gly Ile Asp Ser
1               5                   10                  15

Lys

<210> SEQ ID NO 16
<211> LENGTH: 22
<212> TYPE: PRT
<213> ORGANISM: Artificial Sequence
<220> FEATURE:
<223> OTHER INFORMATION: Peptide incorporating Cyclin D1 degro

<400> SEQUENCE: 16

Lys Ala Ala Glu Glu Glu Glu Ser Leu Ala Ser Thr Pro Thr Asp Val
1               5                   10                  15

Arg Asp Val Asp Ile Lys
            20

<210> SEQ ID NO 17
<211> LENGTH: 17
<212> TYPE: PRT
<213> ORGANISM: Artificial Sequence
<220> FEATURE:
<223> OTHER INFORMATION: Peptide incorporating IFNAR1 degron

<400> SEQUENCE: 17

Lys Lys Tyr Ser Ser Gln Thr Ser Gln Asp Ser Gly Asn Tyr Ser Asn
1               5                   10                  15

Lys

<210> SEQ ID NO 18
<211> LENGTH: 23
<212> TYPE: PRT
<213> ORGANISM: Artificial Sequence
<220> FEATURE:
<223> OTHER INFORMATION: Peptide incorporating p53 degron

<400> SEQUENCE: 18

Lys Pro Leu Ser Ser Ser Val Pro Ser Gln Lys Thr Tyr Gln Gly Ser
1               5                   10                  15

Tyr Gly Phe Arg Leu Gly Lys
            20

<210> SEQ ID NO 19
<211> LENGTH: 23
<212> TYPE: PRT
<213> ORGANISM: Artificial Sequence
<220> FEATURE:
<223> OTHER INFORMATION: Peptide incorporating beta catenin degron

<400> SEQUENCE: 19

Lys Ala Trp Gln Gln Gln Ser Tyr Leu Asp Ser Gly Ile His Ser Gly
1               5                   10                  15

Ala Thr Thr Thr Ala Pro Lys
            20
```

```
<210> SEQ ID NO 20
<211> LENGTH: 1077
<212> TYPE: DNA
<213> ORGANISM: Artificial Sequence
<220> FEATURE:
<223> OTHER INFORMATION: pMD0185 plasmid ORF encoding for a control (no
      degron) YFP-bearing construct

<400> SEQUENCE: 20
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccttcggcta cggcctgcag tgcttcgccc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagct accagtccgc cctgagcaaa gaccccaacg agaagcgcga tcacatggtc     660
ctgctggagt tcgtgaccgc cgccgggatc actctcggca tggacgagct gtacaagagt     720
ggaggcatgt cggctaccgc tgccaccgtc ccgcctgccg ccccggccgg cgagggtggc     780 cccccctgcac ctcctccaaa tcttaccagt aacaggagac tgcagcagac ccaggcccag     840
gtggatgagg tggtggacat catgagggtg aatgtggaca aggtcctgga gcgrgaccag     900
aagctatcgg aactggatga tcgcgcagat gccctccagg caggggcctc ccagtttgaa     960
acaagtgcag ccaagctcaa gcgcaaatac tggtggaaaa acctcaagat gatgatcatc    1020
ttgggagtga tttgcgccat catcctcatc atcatcatcg tttacttcag cacttaa       1077

<210> SEQ ID NO 21
<211> LENGTH: 1077
<212> TYPE: DNA
<213> ORGANISM: Artificial Sequence
<220> FEATURE:
<223> OTHER INFORMATION: pMD0185 ORF encoding for a control/common
      EFP-bearing construct

<400> SEQUENCE: 21
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca cccctgacctg gggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacat cagccacaac gtctatatca ccgccgacaa gcagaagaac     480
ggcatcaagg ccaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
```

| | |
|---|---|
| ctgctggagt tcgtgaccgc cgccgggatc actctcggca tggacgagct gtacaagagt | 720 |
| ggaggcatgt cggctaccgc tgccaccgtc ccgcctgccg cccgcggcgg cgagggtggc | 780 |
| cccctgcac ctcctccaaa tcttaccagt aacaggagac tgcagcagac ccaggcccag | 840 |
| gtggatgagg tggtggacat catgagggtg aatgtggaca aggtcctgga gcgrgaccag | 900 |
| aagctatcgg aactgaataa tcgcgcaaat gccctccagg caggggcctc cgtgtttgaa | 960 |
| acaagtgcag ccaagctcaa gcgcaaatac tggtggaaaa acctcaagat gatgatcatc | 1020 |
| ttgggagtga tttgcgccat catcctcatc atcatcatcg tttacttcag cacttaa | 1077 |

<210> SEQ ID NO 22
<211> LENGTH: 1122
<212> TYPE: DNA
<213> ORGANISM: Artificial Sequence
<220> FEATURE:
<223> OTHER INFORMATION: pMD0189 ORF encoding for a YFP-bearing
      construct having a Bonger degron sequence

<400> SEQUENCE: 22

| | |
|---|---|
| atgggcaaac gtcgccgtgg taacaaatcc ggtggcaagc ttgcaatggt gagcaagggc | 60 |
| gaggagctgt tcaccggggt ggtgcccatc ctggtcgagc tggacggcga cgtaaacggc | 120 |
| cacaagttca gcgtgtccgg cgagggcgag ggcgatgcca cctacggcaa gctgaccctg | 180 |
| aagttcatct gcaccaccgg caagctgccc gtgccctggc ccaccctcgt gaccaccttc | 240 |
| ggctacggcc tgcagtgctt cgcccgctac cccgaccaca tgaagcagca cgacttcttc | 300 |
| aagtccgcca tgcccgaagg ctacgtccag gagcgcacca tcttcttcaa ggacgacggc | 360 |
| aactacaaga cccgcgccga ggtgaagttc gagggcgaca ccctggtgaa ccgcatcgag | 420 |
| ctgaagggca tcgacttcaa ggaggacggc aacatcctgg ggcacaagct ggagtacaac | 480 |
| tacaacagcc acaacgtcta tatcatggcc gacaagcaga agaacggcat caaggtgaac | 540 |
| ttcaagatcc gccacaacat cgaggacggc agcgtgcagc tcgccgacca ctaccagcag | 600 |
| aacacccca tcggcgacgg ccccgtgctg ctgcccgaca ccactaccct gagctaccag | 660 |
| tccgccctga gcaaagaccc caacgagaag cgcgatcaca tggtcctgct ggagttcgtg | 720 |
| accgccgccg ggatcactct cggcatggac gagctgtaca agagtggagg catgtcggct | 780 |
| accgctgcca ccgtcccgcc tgccgccccg gccggcgagg tggccccccc tgcacctcct | 840 |
| ccaaatctta ccagtaacag gagactgcag cagacccagg cccaggtgga tgaggtggtg | 900 |
| gacatcatga gggtgaatgt ggacaaggtc ctggagcgag accagaagct atcggaactg | 960 |
| gatgatcgcg cagatgccct ccaggcaggg gcctcccagt tgaaacaag tgcagccaag | 1020 |
| ctcaagcgca atactggtg gaaaaacctc aagatgatga tcatcttggg agtgatttgc | 1080 |
| gccatcatcc tcatcatcat catcgtttac ttcagcactt aa | 1122 |

<210> SEQ ID NO 23
<211> LENGTH: 1122
<212> TYPE: DNA
<213> ORGANISM: Artificial Sequence
<220> FEATURE:
<223> OTHER INFORMATION: pMD0190 ORF encoding for a YFP-bearing
      construct having an iNOS degron sequence

<400> SEQUENCE: 23

| | |
|---|---|
| atgggcaaag atattaataa caataaatcc ggtggcaagc ttgcaatggt gagcaagggc | 60 |
| gaggagctgt tcaccggggt ggtgcccatc ctggtcgagc tggacggcga cgtaaacggc | 120 |
| cacaagttca gcgtgtccgg cgagggcgag ggcgatgcca cctacggcaa gctgaccctg | 180 |

```
aagttcatct gcaccaccgg caagctgccc gtgccctggc ccaccctcgt gaccaccttc    240
ggctacggcc tgcagtgctt cgcccgctac cccgaccaca tgaagcagca cgacttcttc    300
aagtccgcca tgcccgaagg ctacgtccag gagcgcacca tcttcttcaa ggacgacggc    360
aactacaaga cccgcgccga ggtgaagttc gagggcgaca ccctggtgaa ccgcatcgag    420
ctgaagggca tcgacttcaa ggaggacggc aacatcctgg ggcacaagct ggagtacaac    480
tacaacagcc acaacgtcta tatcatggcc gacaagcaga gaacggcat caaggtgaac     540 ttcaagatcc gccacaacat cgaggacggc agcgtgcagc tcgccgacca ctaccagcag    600
aacaccccca tcggcgacgg ccccgtgctg ctgcccgaca accactacct gagctaccag    660
tccgccctga gcaaagaccc caacgagaag cgcgatcaca tggtcctgct ggagttcgtg    720
accgccgccg ggatcactct cggcatggac gagctgtaca agagtggagg catgtcggct    780
accgctgcca ccgtcccgcc tgccgccccg gccggcgagg gtggccccc tgcacctcct    840 ccaaatctta ccagtaacag gagactgcag cagacccagg cccaggtgga tgaggtggtg    900
gacatcatga gggtgaatgt ggacaaggtc ctggagcgag accagaagct atcggaactg    960
gatgatcgcg cagatgccct ccaggcaggg gcctcccagt ttgaaacaag tgcagccaag   1020
ctcaagcgca aatactggtg gaaaaacctc aagatgatga tcatcttggg agtgatttgc   1080
gccatcatcc tcatcatcat catcgtttac ttcagcactt aa                     1122
```